(12) United States Patent
Johnson et al.

(10) Patent No.: US 7,329,517 B2
(45) Date of Patent: Feb. 12, 2008

(54) **ESCAPIN PROTEIN, A BROADLY ANTIMICROBIAL COMPOUND FROM INK OF THE SEA HARE *APLYSIA CALIFORNICA*, AND USES THEREOF**

(76) Inventors: Paul Micah Johnson, 10891 Arbour Dr., Brighton, MI (US) 48114; Hsiuchin Yang, 3071 Hudson Way, Decatur, GA (US) 30033; Charles D. Derby, 2798 Rangewood Dr., Atlanta, GA (US) 30345; Phang C. Tai, 2835 Cravey Dr., Atlanta, GA (US) 30345

( * ) Notice: Subject to any disclaimer, the term of this patent is extended or adjusted under 35 U.S.C. 154(b) by 0 days.

(21) Appl. No.: 11/100,328

(22) Filed: Apr. 6, 2005

(65) Prior Publication Data

US 2006/0051337 A1    Mar. 9, 2006

Related U.S. Application Data

(60) Provisional application No. 60/561,115, filed on Apr. 9, 2004.

(51) Int. Cl.
    *C12N 9/00*    (2006.01)
(52) U.S. Cl. .................. 435/189; 435/183; 435/69.1
(58) Field of Classification Search .............. 530/350
     See application file for complete search history.

(56) References Cited

FOREIGN PATENT DOCUMENTS

EP            03001232    *    1/2003

OTHER PUBLICATIONS

Nolen et al., Ink secretion by the marine snail *Aplysia californica* enhances its ability to escape from a natural predator, J Comp Physiol A, 1995, 175, pp. 239-254.*
Ngo et al. in The Protein Folding Problem and Tertiary Structure Prediction, 1994, Merz et al. (ed.), Birkhauser, Boston, MA, pp. 433 and 492-495.*
Abrahmsen, L., et al., 1991, "Engineering Subtilisin and Its Substrates for Efficient Ligation of Peptide Bonds in Aqueous Solution," *Biochemistry*, 30:4151-4159.
Baggiolini, M., et al., 1992, "Interleukin-8, a chemotactic and inflammatory cytokine," *FEBS Lett*. 307-97-101.
Balaban, N. Q., et al., 2004, "Bacterial persistence as a phenotypic switch," *Science* 305:1622-1625.
Butzke, D., et al., 2004, "Hydrogen peroxide produced by *Aplysia* ink toxin kills tumor cells independent of apoptosis via peroxiredoxin I sensitive pathways." *Cell Death Differ*. 11:608-617.
Chapman, D. J., et al., 1969, "Bile pigment metabolism in the sea-hare *Aplysia*," *J. Exp. Mar. Biol. Ecol*. 4:71-78.
Clark-Lewis, I., et al., 1994, "Structural Requirements for Interleukin-8 Function Identified by Design of Analogs and CXC Chemokine Hybrids," *J. Biol.Chem.*, 269:16075-16081.
Clark-Lewis I., et al., 1991, "Chemical Synthesis, Purification, and Characterization of Two Inflammatory Proteins, Neutrophil Activating Peptide 1 (Interleukin-8) and Neutrophil Activating Peptide 2," *Biochemistry*, 30:3128-3135.
Dawson, et al., 1994, "Synthesis of Proteins by Native Chemical Ligation," *Science*, 266:776-779.
deLisle Millton, R.C., et al., "Synthesis and Proteins by Chemical Ligation of Unprotected Peptide Segments: Mirror-Image Enzyme Molecules, D- & L-HIV Protease Analogs," *Techniques in Protein Chemistry IV*. Academic Press, NY, 1993; 257-267.
Ehara, T., et al., 2002, "Antimicrobial action of achacin is mediated by L-amino acid oxidase activity," *FEBS Lett*. 531:509-512.
Iguchi, S.M., et al., 1982, "Antibacterial activity of snail mucus mucin," *Comp. Biochem. Physiol*. 72A(3):571-574.
Iijima, R., et al., 1995, "Antifungal activity of aplysianin E, a cytotoxic protein of sea hare (*Aplysia kurodai*) eggs," *Dev. Comp. Immunol*. 19(1):13-19.
Iijima, R., et al., 2003, "L-Amino acid oxidase activity of an antineoplastic factor of a marine mollusk and its relationship to cytotoxicity," *Dev. Comp. Immunol*. 27:505-512.
Jaeger, J.A., et al., 1989, "Improved Predictions of Secondary Structures for RNA," *Proc. Natl. Acad. Sci. USA*. 86:7706-7710.
Jaeger, J.A., et al., 1989, "Predicting Optimal and Suboptimal Secondary Structure for RNA," *Methods in Enzymol*. 183:281-306.
Jimbo, M., et al., 2003, "Characterization of L-amino acid oxidase and antimicrobial activity of aplysianin A, a sea hare-derived antitumor-antimicrobial protein," *Fisheries Sci*. 69:1240-1246.
Johnson, P.M., 2002, "Multi-component chemical defense in seahares (Gastropoda: Opisthobranchia): antipredator compounds act as both honest and deceptive signals to multiple predator species," *Dissertation*, University of Washington.
Johnson, P.M., et al., 1999, "Defense in sea hares (Gastropoda, Opisthobranchia, Anaspidea): multiple layers of protection from egg to adult," *Mar. Freshwat. Behav. Physiol*. 32:147-180.
Kamiya, H., et al., 1989, "Purification of characterization of an antibacterial and antineoplastic protein secretion of a sea hare, *Aplysia juliana*," *Toxicon* 27:1268-1277.
Kamiya, H., et al., 1986, "Aplysianin-A, an antibacterial and antineoplastic glycoprotein in the albumen gland of a sea hare, *Aplysia kurodai*," *Experientia* 42:1065-1067.
Kanzawa, N., et al., 2004, "Achacin induces cell death in HeLa cells through two different mechanisms," *Arch. Biochem. Biophys*. 422:103-109.
Keren, I., et al., 2004, "Persister cells and tolerance to antimicrobials," *FEMS Microbiol. Lett*. 230:13-18.

(Continued)

*Primary Examiner*—Richard Hutson
*Assistant Examiner*—Jae Wan Lee
(74) *Attorney, Agent, or Firm*—Needle & Rosenberg, P.C.

(57) ABSTRACT

The present invention provides an isolated polypeptide (escapin), and fragments thereof, from the sea hare *Aplysia californica* that have antimicrobial action directed against fungi, yeast, bacteria, and cyanobacteria. Further, the present invention provides an isolated nucleic acid, and fragments thereof, that encode the polypeptide and fragments thereof. Also provided are primers for detecting the nucleic acids of the present invention. A method of inhibiting microbial growth and inhibiting biofilm formation on a surface is also provided.

5 Claims, 14 Drawing Sheets

OTHER PUBLICATIONS

Kisugi, J., et al., 1989, "Biopolymers from marine invertebrates. X. Mode of action of an antibacterial glycoprotein, aplysianin E, from eggs of a sea hare, *Aplysia kurodai*," *Chem. Pharm. Bull. (Tokyo)* 37:3050-3053.

Kubota, Y., et al., 1985, "Purification and characterization of an antibacterial factor from snail mucus," *Comp. Biochem. Physiol.* 82C:345-348.

Light, D.R., et al., 1980, "Analytical and preparative high-performance liquid chromatography separation of flavin and flavin analog coenzymes," *Anal. Biochem.* 109:87-93.

Lu, Q.M., et al., 2002, "L-amino acid oxidase from *Trimeresurus jerdonii* snake venom: purification, characterization, platelet aggregation-inducing and antibacterial effects," *J Nat Toxins* 11(4):345-352.

MacColl, R., et al., 1990, "The chromophore and polypeptide composition of *Aplysia* ink," *Biol. Bull.* 179:326-331.

Macheroux, P., et al., 2001, "L-Amino-acid oxidase from the Malayan pit viper *Calloselasma rhodostoma*: Comparative sequence analysis and characterization of active and inactive forms of the enzyme," *Eur. J. Biochem.* 268:1679-1686.

Melo, V. M., et al., 2000, "Purification of a novel antibacterial and haemagglutinating protein from the purple gland of the sea hare, *Aplysia dactylomela*," Rang, 1828. *Toxicon* 38:1415-1427.

Melo, V. M., et al., 1998, "Toxic, antimicrobial and hemagglutinating activities of the purple fluid of the sea hare *Aplysia dactylomela*," Rang, 1828. *Braz. J. Med. Biol. Res.* 31:785-791.

Nolen, T. G., et al., 1995, "Ink secretion by the marine snail *Aplysia californica* enhances its ability to escape from a natural predator," *J. Comp. Physiol.* A 176:239-254.

Obara, K., et al., 1992, "Molecular cloning of the antibacterial protein of the giant African snail, *Achatina fulica* Ferussac," *Eur. J. Biochem.* 209:1-6.

Ogawa, M., et al., 1999, "Macromolecular antimicrobial glycoprotein, achacin, expressed in a methylotrophic yeast *Pichia pastoris*," *FEBS Lett.* 448:41-44.

Otsuka-Fuchino, H., et al., 1993, "Morphological aspects of achacin-treated bacteria," *Comp. Biochem. Physiol.* 104C:37-42.

Otsuka-Fuchino, H., et al., 1992, "Bactericidal action of a glycoprotein from the body surface mucus of giant African snail," *Comp. Biochem. Physiol.* 101C:607-613.

Petzelt, C., et al., 2002, "Cytotoxic cyplasin of the sea hare, *Aplysia punctata*, cDNA cloning, and expression of bioactive recombinants in insect cells," *Neoplasia* 4:49-59.

Rajarathnam, K., et al., 1994, "$^1$H NMR Studies of Interleukin 8 Analogs: Characterization of the Domains Essential for Function," *Biochemistry* 33:6623-6630.

Smith, M. 1985, "In Vitro Mutagenesis," *Ann. Rev. Gen.*, 19:423-462.

Torii, S., et al., 2000, "Molecular cloning and functional analysis of apoxin I, a snake venom-derived apoptosis-inducing factor with L-amino acid oxidase activity," *Biochemistry* 39:3197-3205.

Troxler, R.R., et al., 1981, "Structural studies on aplysioviolin," *Biol. Bull.* 161:339 (abstract).

Wei, J., et al., 2003, "Purification, characterization and biological activity of an L-amino acid oxidase from *Trimeresurus mucrosquamatus* venom," *Acta Biochimica et Biophysica Sinica (Shanghai) ISSN 0582-9879*, 35:219-224.

Whitby, L.G., 1953, "A New Method for Preparing Flavin-adenine Dinucleotide," *Biochem. J.* 54:437-442.

Yamazaki, M., 1993, "Antitumor and antimicrobial glycoproteins from sea hares," *Comp. Biochem. Physiol.* 105C:141-146.

Yamazaki, M., et al., 1989, "Isolation and characterization of a novel cytolytic factor in purple fluid of the sea hare, *Aplysia kurodai*," *Cancer Res.* 49:3834-3838.

Yamazaki, M., et al., 1989, "Purification and characterization of a cytolytic protein from purple fluid of the sea hare," *Dolabella auricularia. Chem. Pharm. Bull.* (Tokyo) 37:2179-2182.

Yamazaki, M., et al., 1990, "Bacteriostatic and cytolytic activity of purple fluid from the sea hare," *Dev. Comp. Immunol.* 14(4):379-383.

Zoller, M.J., 1991, "New molecular biology methods for protein engineering," *Curr. Opin. Struct. Biol.*, 1:605-610.

Zuker, M., 1989, "On Finding All Suboptimal Foldings of an RNA Molecule," *Science* 244(4900):48-52.

\* cited by examiner

ESCAPIN PROTEIN, A BROADLY ANTIMICROBIAL COMPOUND FROM INK OF THE SEA HARE *APLYSIA CALIFORNICA*, AND USES THEREOF

CROSS REFERENCE TO RELATED APPLICATIONS

This application claims the benefit of U.S. Provisional Patent Application No. 60/561,115, filed Apr. 9, 2004, which application is hereby incorporated by this reference in its entirety.

ACKNOWLEDGMENTS

This invention was made with government support under Grants IBN-0324435 and IBN-9876754 awarded by the National Science Foundation. The government has certain rights in the invention.

BACKGROUND OF THE INVENTION

1. Field of the Invention

This invention relates generally to proteins secreted by marine opisthobranch gastropod mollusks known as sea hares. Specifically, the invention relates to a novel protein, fragments thereof, nucleotide sequences that encode the protein and fragments thereof, derived from the sea hare *Aplysia californica,* and methods of use thereof. The novel protein is referred to herein as "escapin."

2. Background Art

Ink from some species of sea hares has been shown to have antipredatory and antimicrobial effects. The active component of the ink in the sea hare *Aplysia californica* has not been previously identified or characterized. The present invention provides the active component of the ink in the sea hare *Aplysia californica* and methods of use thereof.

SUMMARY OF THE INVENTION

In accordance with the purposes of this invention, as embodied and broadly described herein, this invention, in one aspect, relates to an isolated polypeptide comprising SEQ ID NO:1.

In another aspect, the invention relates to an isolated polypeptide comprising a fragment of the polypeptide identified as SEQ ID NO:1.

In yet another aspect, the invention relates to an isolated polypeptide comprising the amino acid sequence identified as SEQ ID NO:1 with one or more conservative amino acid substitutions.

In another aspect, the invention relates to an isolated polypeptide consisting of SEQ ID NO:1.

In another aspect, the invention relates to an isolated fragment of the polypeptide identified as SEQ ID NO:1 with one or more conservative amino acid substitutions.

In another aspect, the invention relates to an isolated nucleic acid identified as SEQ ID NO:2.

In another aspect, the invention relates to an isolated fragment of the nucleic acid identified as SEQ ID NO:2.

In another aspect, the invention relates to a method of inhibiting growth of a microbe on a surface, comprising contacting the surface with a polypeptide or fragment thereof of the invention, whereby growth of the microbe is inhibited by the polypeptide or fragment thereof on the surface.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The present invention provides a novel, naturally occurring polypeptide and fragment thereof derived from the ink of *A. californica* that can prevent the growth of fungi, yeast, bacteria, and cyanobacteria on various surfaces, including, but not limited to, medical devices and instruments, toys, bathroom and kitchen surfaces, floors, and the underside of ships.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 2A and 2B shows amino acid sequence alignment of escapin (SEQ ID NO:1) and related proteins (SEQ ID NOs:24-29). Solid underline and dashed line indicate DMB and GG motifs, respectively. * indicates the predicted signal sequence cleavage site at A 18 and D 19. ** indicates the predicted glycosylation site at Thr 643.

DESCRIPTION OF THE PREFERRED EMBODIMENTS

Figure 1:
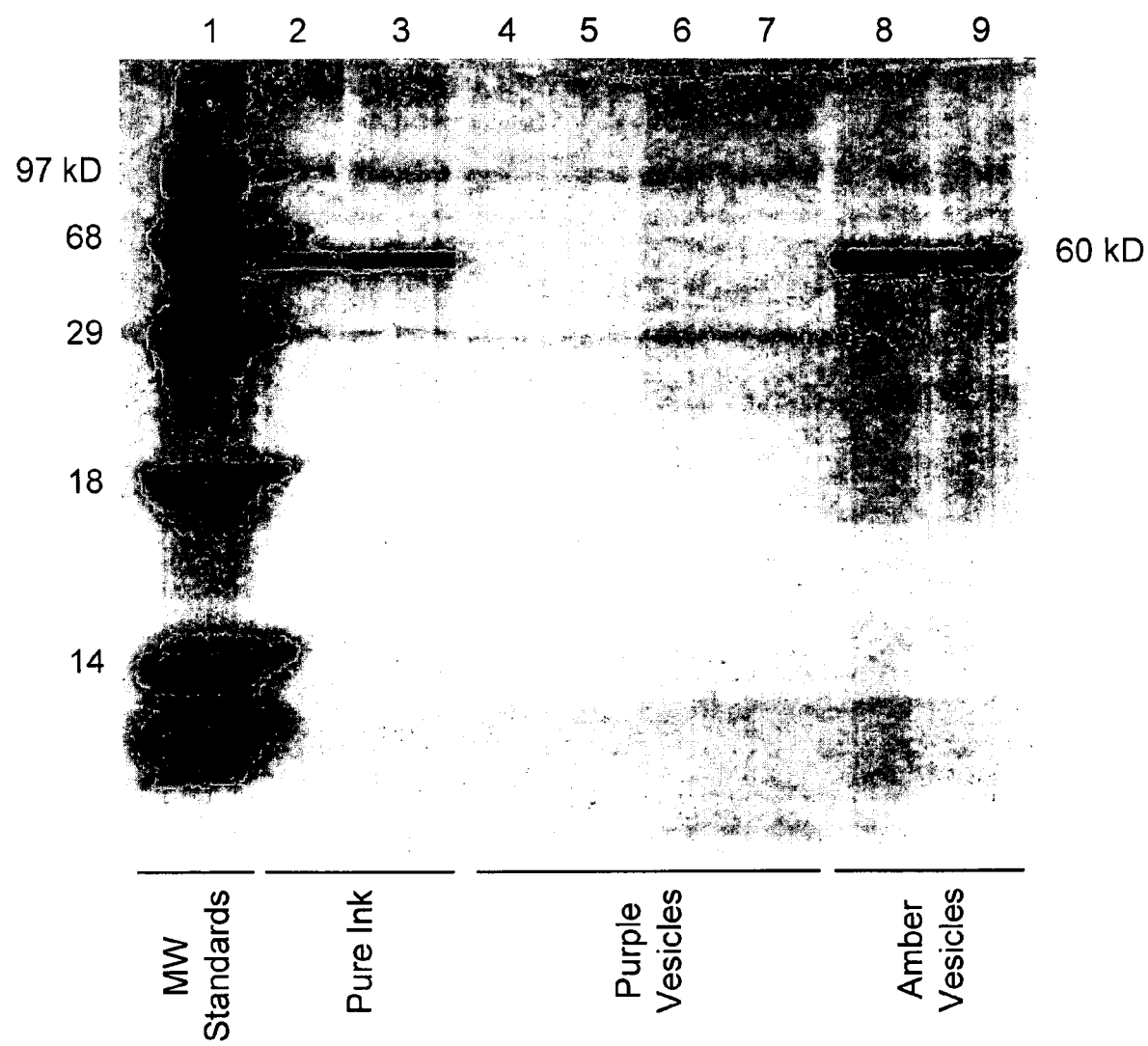
FIG. 1 shows that SDS-PAGE shows the dominant ink protein, escapin, localized in amber vesicles. Lane 1: Standards—97, 68, 29, 18 and 14 kDa; Lanes 2-3: pure ink showing major band at~60 kDA; Lanes 4-7: purple vesicles showing no major band; Lanes 8-9: amber vesicles showing major band at ~60 kDa.
Figure 3:
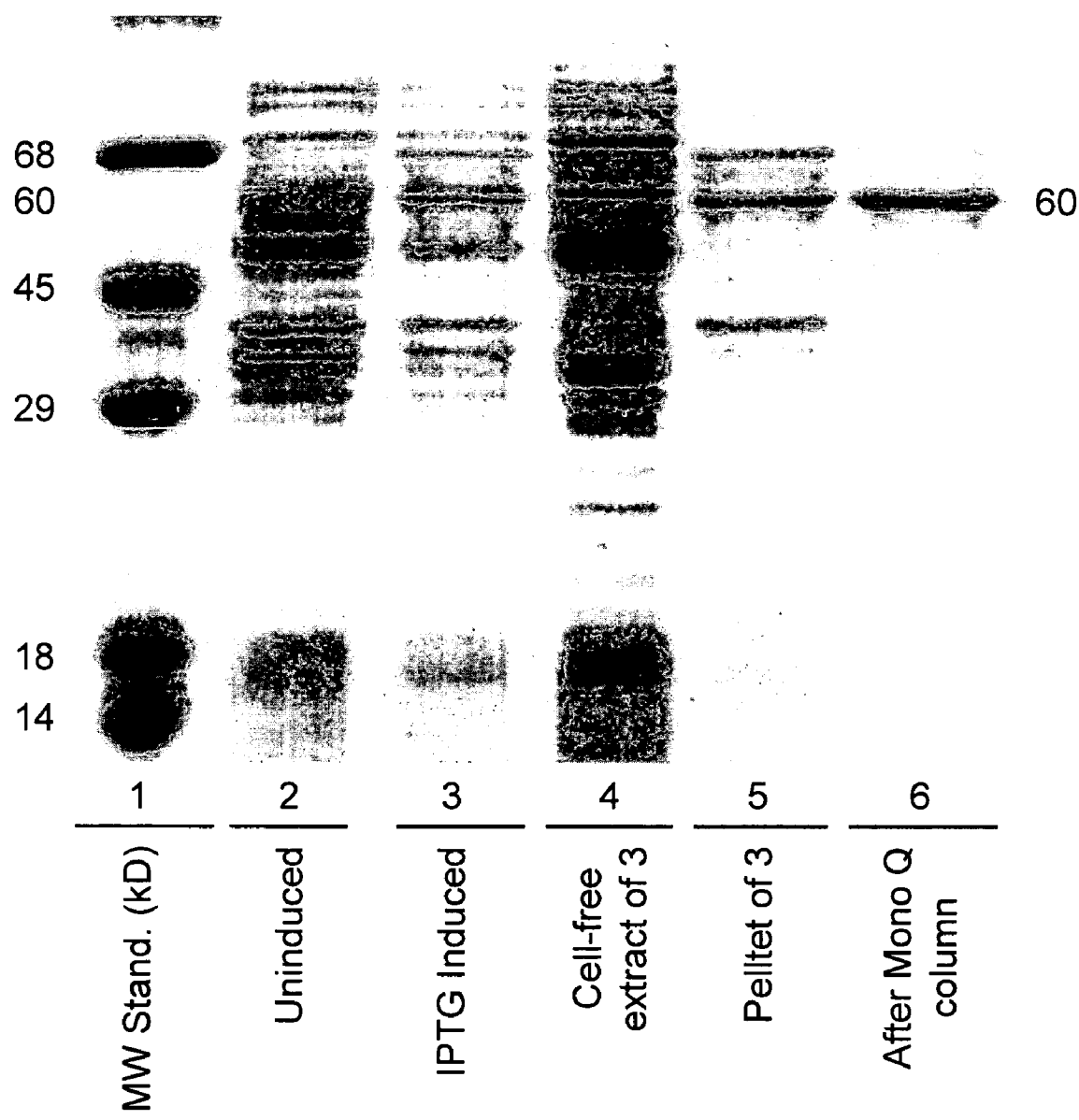
FIG. 3 shows over-expression of escapin in *E. coli.* Lane 1: Standards—68, 45, 29, 18, and 14 kDa; 2: uninduced; 3: IPTG induced; 4: cell-free extract of 3; 5: pellet of 3; 6: after Mono Q purification—showing predominant 60 kDa protein.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific amino acid sequences and nucleotide sequences, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to a polypeptide includes mixtures of polypeptides.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings: "Optional" or "optionally" means that the subsequently described event or circumstance may or may not occur, and that the description includes instances where said event or circumstance occurs and instances where it does not.

Polypeptides

The present invention provides an isolated polypeptide comprising SEQ ID NO:1. Further provided is an isolated polypeptide comprising a fragment of the polypeptide identified as SEQ ID NO:1. An example of a fragment of the polypeptide identified as SEQ ID NO:1 is the fragment having an amino acid sequence identified as SEQ ID NO:19 which is the full-length protein without a signal peptide. The molecular weight of this fragment is about 58-60 kDa. Another example of a fragment of the polypeptide identified as SEQ ID NO:1 is an N-terminal fragment having a molecular weight of about 34 kDa and the amino acid sequence identified as SEQ ID NO:21 The fragments of the invention have anti-microbial activity and can be antigenic. Also provided is an isolated polypeptide comprising the amino acid sequence identified as SEQ ID NO:1 with one or more conservative amino acid substitutions. The present invention also provides an isolated polypeptide consisting of SEQ ID NO:1.

By "isolated polypeptide" or "purified polypeptide" is meant a polypeptide that is substantially free from the materials with which the polypeptide is normally associated in nature or in culture. The polypeptides of the invention can be obtained, for example, by extraction from a natural source, for example, a sea hare, by expression of a recombinant nucleic acid encoding the polypeptide (for example, in a cell or in a cell-free translation system), or by chemically synthesizing the polypeptide. In addition, a polypeptide may be obtained by cleaving full-length polypeptides. When the polypeptide is a fragment of a larger naturally occurring polypeptide, the isolated polypeptide is shorter than and excludes the full-length, naturally-occurring polypeptide of which it is a fragment.

The polypeptides of the invention can be prepared using any of a number of chemical polypeptide synthesis techniques well known to those of ordinary skill in the art including solution methods and solid phase methods. One method of producing the polypeptides of the present invention is to link two or more peptides or polypeptides together by protein chemistry techniques. For example, peptides or polypeptides can be chemically synthesized using currently available laboratory equipment using either Fmoc (9-fluorenylmethyloxy-carbonyl) or Boc (tert-butyloxycarbonoyl) chemistry (Applied Biosystems, Inc., Foster City, Calif.). One skilled in the art can readily appreciate that a peptide or polypeptide corresponding to the antibody of the present invention, for example, can be synthesized by standard chemical reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin-8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with fill biological activity (deLisle Milton R C et al., Techniques in Protein Chemistry IV. Academic Press, New York, pp. 257-267 (1992)).

The polypeptides of the invention can also be prepared by other means including, for example, recombinant techniques. Examples of appropriate cloning and sequencing techniques, and instructions sufficient to direct persons of skill through many cloning exercises are found in Sambrook et al. (1989) Molecular Cloning: A Laboratory Manual (2nd ed.) Vol. 1-3, Cold Spring Harbor Laboratory, Cold Spring Harbor Press, NY, (Sambrook).

Also provided by the present invention is a polypeptide comprising an amino acid sequence at least about 70%, 75%, 80%, 85%, 90%, 91%, 92%, 93%, 94%, 95%, 96%, 97%, 98% or 99% identical to a sequence consisting of SEQ ID NO: 1.

It is understood that as discussed herein the use of the terms "homology" and "identity" mean the same thing as similarity. Thus, for example, if the use of the word homology is used to refer to two non-natural sequences, it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related.

In general, it is understood that one way to define any known variants and derivatives or those that might arise, of the disclosed nucleic acids and polypeptides herein, is through defining the variants and derivatives in terms of homology to specific known sequences. In general, variants of nucleic acids and polypeptides herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two polypeptides or nucleic acids. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/bl2seq/bl2.html), or by inspection.

The same types of homology can be obtained for nucleic acids by, for example, the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Also provided by the present invention is a polypeptide comprising an amino acid sequence selected from the group consisting of SEQ ID NO: 1, with one or more conservative amino acid substitutions. These conservative substitutions are such that a naturally occurring amino acid is replaced by one having similar properties. Such conservative substitutions do not alter the function of the polypeptide. For example, conservative substitutions can be made according to the following table, Table 1:

TABLE 1

Amino Acid Substitutions

| Original Residue | Exemplary Substitutions |
|---|---|
| Arg | Lys |
| Asn | Gln |
| Asp | Glu |
| Cys | Ser |
| Gln | Asn |
| Glu | Asp |
| Gly | Pro |
| His | Gln |
| Ile | leu; val |
| Leu | ile; val |
| Lys | arg; gln |
| Met | leu; ile |
| Ser | Thr |
| Thr | Ser |
| Trp | Tyr |
| Tyr | trp; phe |
| Val | ile; leu |

Thus, it is understood that, where desired, modifications and changes may be made in the nucleic acid encoding the polypeptides of this invention and/or amino acid sequence of the polypeptides, or fragments thereof, of the present invention and still obtain a polypeptide having like or otherwise desirable characteristics. Such changes may occur in natural isolates or may be synthetically introduced using site-specific mutagenesis, the procedures for which, such as mismatch polymerase chain reaction (PCR), are well known in the art. For example, certain amino acids may be substituted for other amino acids in a polypeptide without appreciable loss of functional activity. It is thus contemplated that various changes may be made in the amino acid sequence of the polypeptides or fragments of the present invention (or underlying nucleic acid sequence) without appreciable loss of biological utility or activity and possibly with an increase in such utility or activity.

Further provided by the invention are antigenic fragments of the polypeptide identified as SEQ ID NO: 1. Examples of antigenic fragments include, but are not limited to, amino acid sequences identified as SEQ ID NOs:19 and 21.

Nucleic Acids

The present invention provides an isolated nucleic acid encoding the polypeptide identified as having amino acid sequence SEQ ID NO:1; this nucleic acid is identified in the sequence listing as SEQ ID NO:2. Further provided is an isolated nucleic acid comprising the nucleic acid identified as SEQ ID NO:2. Also provided is a fragment of the nucleic acid identified as SEQ ID NO:2. Examples of fragments of the nucleic acid identified as SEQ ID NO:2 include, but are not limited to, a nucleic acid having the nucleic acid sequence identified as SEQ ID NO:20 that encodes a polypeptide of the invention identified as SEQ ID NO:19, and a nucleic acid having the nucleic acid sequence identified as SEQ ID NO:22 that encodes a polypeptide of the invention identified as SEQ ID NO:21.

The present invention also provides primers/probes that can be used with various methods known in the art, for example PCR, to identify a polypeptide of the present invention. Examples of these primers include, but are not limited to, nucleic acids with the sequences identified as SEQ ID NOs:3-18.

As used herein, the term "nucleic acid" refers to single or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the moieties discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides), a reduction in the AT content of AT rich regions, or replacement of non-preferred codon usage of the expression system to preferred codon usage of the expression system.

The nucleic acid can be directly cloned into an appropriate vector, or if desired, can be modified to facilitate the subsequent cloning steps. Such modification steps are routine, an example of which is the addition of oligonucleotide linkers which contain restriction sites to the termini of the nucleic acid. General methods are set forth in Sambrook et al., "Molecular Cloning, a Laboratory Manual," Cold Spring Harbor Laboratory Press (1989).

Once the nucleic acid sequence is obtained, the sequence encoding the specific amino acids can be modified or changed at any particular amino acid position by techniques well known in the art. For example, PCR primers can be designed which span the amino acid position or positions and which can substitute any amino acid for another amino acid. Alternatively, one skilled in the art can introduce specific mutations at any point in a particular nucleic acid sequence through techniques for point mutagenesis. General methods are set forth in Smith, M. "In vitro mutagenesis" Ann. Rev. Gen., 19:423-462 (1985) and Zoller, M. J. "New molecular biology methods for protein engineering" Curr. Opin. Struct. Biol., 1:605-610 (1991), which are incorporated herein in their entirety for the methods. These techniques can be used to alter the coding sequence without altering the amino acid sequence that is encoded.

Vectors, Cells, and Methods of Using

Also provided is a vector, comprising a nucleic acid of the present invention. The vector can direct the in vivo or in vitro synthesis of any of the polypeptides described herein.

The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.). The vector, for example, can be a plasmid. The vectors can contain genes conferring hygromycin resistance, gentamicin resistance, or other genes or phenotypes suitable for use as selectable markers, or methotrexate resistance for gene amplification. The vector can comprise the nucleic acid in pET15b, pSRα-Neo, pPICZα, or pPIC9K.

There are numerous other *Escherichia coli* (*E. coli*) expression vectors, known to one of ordinary skill in the art, which are useful for the expression of the nucleic acid insert. Other microbial hosts suitable for use include bacilli, such as *Bacillus subtilis,* and other enterobacteriaceae, such as *Salmonella, Serratia,* and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures. Also, nucleic acid modifications can be made to promote amino terminal homogeneity.

Additionally, yeast expression can be used. The invention provides a nucleic acid encoding a polypeptide of the present invention, wherein the nucleic acid can be expressed by a yeast cell. More specifically, the nucleic acid can be expressed by *Pichia pastoris* or *Saccharomyces cerevisiae*. There are several advantages to yeast expression systems, which include, for example, *S. cerevisiae* and *P. pastoris*. First, evidence exists that proteins produced in yeast secretion systems exhibit correct disulfide pairing. Second, efficient large-scale production can be carried out using yeast expression systems. The *S. cerevisiae* pre-pro-alpha mating factor leader region (encoded by the MFα-1 gene) can be used to direct protein secretion from yeast. The leader region of pre-pro-alpha mating factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha mating factor leader region. This construct can be put under the control of a strong transcription promoter, such as the alcohol dehydrogenase I promoter, alcohol oxidase I promoter, a glycolytic promoter, or a promoter for the galactose utilization pathway. The nucleic acid coding sequence is followed by a translation termination codon which is followed by transcription termination signals.

Alternatively, the nucleic acid coding sequences can be fused to a second protein coding sequence, such as Sj26 or beta-galactosidase, used to facilitate purification of the fusion protein by affinity chromatography. The insertion of protease cleavage sites to separate the components of the fusion protein is applicable to constructs used for expression in yeast. Efficient post-translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, genticin or G418 resistance, or other genes or phenotypes suitable for use as selectable markers, or methotrexate resistance for gene amplification. The chimeric protein coding sequence can be introduced into a Chinese hamster ovary (CHO) cell line using a methotrexate resistance encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well known methods, which vary depending on the type of cellular host. For example, calcium chloride transformation is commonly utilized for prokaryotic cells, whereas calcium phosphate, DEAE dextran, or lipofectin mediated transfection or electroporation may be used for other eukaryotic cellular hosts.

Alternative vectors for the expression of genes or nucleic acids in mammalian cells, those similar to those developed for the expression of human gamma interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acids in mammalian cells (such as COS 7).

Insect cells, for example, can also permit the expression of various proteins. Recombinant proteins produced in insect cells with baculovirus vectors undergo post-translational modifications similar to that of wild-type proteins. Briefly, baculovirus vectors useful for the expression of active proteins in insect cells are characterized by insertion of the protein coding sequence downstream of the *Autographica californica* nuclear polyhedrosis virus (AcNPV) promoter for the gene encoding polyhedrin, the major occlusion protein. Cultured insect cells such as *Spodoptera frugiperda* cell lines are transfected with a mixture of viral and plasmid DNAs and the viral progeny are plated. Deletion or insertional inactivation of the polyhedrin gene results in the production of occlusion-negative viruses which form plaques that are distinctively different from those of wild-type occlusion-positive viruses. These distinctive plaque morphologies allow visual screening for recombinant viruses in which the AcNPV gene has been replaced with a hybrid gene of choice.

Also provided are the vectors containing the contemplated nucleic acids in a host suitable for expressing the nucleic acids. The host cell can be a prokaryotic cell, including, for example, a bacterial cell. More particularly, the bacterial cell can be an $E.\ coli$ cell. Alternatively, the cell can be a eukaryotic cell, including, for example, a Chinese hamster ovary (CHO) cell, a myeloma cell, a Pichia cell, or an insect cell. The coding sequence for any of the polypeptides described herein can be introduced into an insect cell line, for example, using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines have been developed and include myeloma cell lines, fibroblast cell lines, and a variety of tumor cell lines such as melanoma cell lines. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

Further provided is a method of making any of the polypeptides or fragments thereof of the present invention, comprising culturing a host cell comprising a vector that encodes a polypeptide or fragment thereof and purifying the polypeptide or fragment thereof produced by the host cell. As mentioned above, these polypeptides include, but are not limited to, a polypeptide comprising SEQ ID NO: 1 or fragments thereof. The polypeptides of the present invention can also be made by culturing a host cell comprising a nucleic acid that encodes the full-length Escapin protein (SEQ ID NO:1), purifying the full-length Escapin protein produced by the host cell and digesting the full-length Escapin protein with the appropriate enzymes to produce a polypeptide comprising a fragment of SEQ ID NO:1.

Antibodies

Provided is an isolated antibody or fragment thereof that specifically binds an epitope contained in the Escapin protein. In other words, the present invention provides an isolated antibody or fragment thereof that specifically binds an epitope contained within the amino acid sequence identified as SEQ ID NO:1.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse or other species. The heavy chain constant domains that correspond to the different classes of immunoglobulins are called alpha, delta, epsilon, gamma, and mu, respectively.

As used herein, the terms "immunoglobulin heavy chain or fragments thereof" and "immunoglobulin light chain or fragments thereof" encompass chimeric peptides and hybrid peptides, with dual or multiple antigen or epitope specificities, and fragments, including hybrid fragments. Thus, fragments of the heavy chains and/or fragments of the light chains that retain the ability to bind their specific antigens are provided. For example, fragments of the heavy chains and/or fragments of the light chains that maintain Escapin protein binding activity are included within the meaning of the terms "immunoglobulin heavy chain or fragments thereof" and "immunoglobulin light chain and fragments thereof," respectively. Such heavy chains and light chains and fragments thereof, respectively, can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Further provided is a method of inhibiting growth of a microbe on a surface, comprising contacting the surface with the polypeptide of the invention, whereby growth of the microbe is inhibited by the polypeptide on the surface. Examples of a surface include, but are not limited to, medical devices and instruments, toys, bathroom and kitchen surfaces, floors, and the underside of ships. A surface can be contacted with a polypeptide of the invention by methods known to a person of skill. Such methods include, but are not limited to, brushing, spraying, dipping, and immersing. The inhibition of growth of microbes on a surface can prevent formation of biofilm. Examples of microbes whose growth can be inhibited by the polypeptide of the present invention include, but are not limited to, fungi, yeast, bacteria, and cyanobacteria.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

Example 1

Animals. Sea hares, *Aplysia californica*, were collected in California or provided by the NIH National Resource for *Aplysia* Facility (http://www.rsmas.miami.edu/groups/seahares/). They were maintained in aquaria containing recirculating, filtered, and aerated artificial sea water (Instant Ocean™: Aquarium Systems), and fed red alga (*Gracilaria ferox*).

Ink gland processing. The ink glands were surgically removed from sea hares, gently squeezed in a Petri dish with the blunt end of a scalpel handle to release most of the ink secretion from the individual vesicles contained in the gland. The secretion was then pipetted to a microfuge tube and frozen at −80° C. until needed.

Opaline gland processing. The opaline glands were surgically removed from sea hares, gently blotted dry on a Kimwipe® to remove seawater (since water causes opaline secretion to polymerize) and transferred to an ultracentrifuge tube. This was centrifuged at 30,000 g for 30 min at 4° C. (Beckman Optima TLX Ultracentrifuge). The pure opaline was then pipetted away from the gland tissue, transferred to a microfuge tube, and frozen at −80° C. until needed.

Purification of proteins from purple ink. Proteins were isolated and purified using an ÄKTA 100 Automated FPLC (Amersham Pharmacia Biotech). A preparative grade Hi-Load Superdex 200 16/60 column (Pharmacia) or an in-house-packed Sephacryl 300 HR 26/60 column was used for initial size separation with fractions collected in an automated fraction collector. Fractions identified to have activity by bacterial assay were concentrated using a Biomax 5K NMWL membrane Ultrafree Centrifugal Filter Device (Millipore). Active fractions were further purified on a cation exchange Mono S column, and fractions were collected, assayed, concentrated, and frozen at −80° C. One purified protein of interest was named "escapin" and was bright yellow. Escapin's concentration was determined by Bradford assay using bovine serum albumen (BSA) as a standard. The molecular mass of purified escapin was determined by gel filtration using a Superose-6 10/30 column (Amersham Pharmacia Biotech) eluted with 50 mM potassium phosphate buffer (pH 7.2) containing 150 mM KCl at a flow rate of 0.5 ml/min. The molecular weight markers were BSA (67 kDa), ovalbumen (43 kDa), and chymotrypsinogen A (25 kDa).

Protein sequencing. *Aplysia californica* ink was analyzed for protein content using sodium dodecyl sulfate polyacrylamide gel electrophoresis (SDS-PAGE) on 12% gels. A single dominant protein band was found at about 60,000 Daltons and was found to be escapin. This band was blotted from the polyacrylamide gel to a PVDF membrane using CAPS transfer buffer and determined by protein microsequencing and proteomic mass spectrometry (University of Massachusetts Medical School Proteomic Mass Spectrometry Lab: http://www.umassmed.edu/proteomic/leszyk). After identifying peptide fragments from escapin, a BLAST search was conducted to find homologous protein fragments. N-terminal sequence of escapin was performed at the Georgia State University Protein Sequencing Facility using a protein sequencer (Procise 492; Applied Biosystems).

mRNA extraction and RT-PCR. To isolate intact mRNA from *A. californica* ink glands without degradation of mRNA, animals were dissected in $MgCl_2$/DEPC solution isotonic with sea water in a 4° C. cold room. Ink glands were removed and immediately transferred to liquid $N_2$. Glands were ground with a mortar and pestle while still in liquid $N_2$. This material was transferred to an RNase-free tube, and mRNA was isolated following the manufacturer's protocols (Roche mRNA Isolation Kit, Cat. No. 1-741-985). Two primers from the N-terminal sequence (TTCGAGTTCTGC-GACCGGGT) (SEQ ID NO:11) and C-terminal sequence (CCAAGGCTGGTCAAAGGTCA) (SEQ ID NO:15) of cyplasin L (Accession #AJ304802) were designed based on the results of homologous sequences recovered following the BLAST search. Primers were used for RT-PCR following the manufacturer's protocols (Roche Titan One Tube RT-PCR System, Best Nr. 1-888-382) using an Eppendorf Mastercycler Gradient thermocycler. The resultant RT-PCR product, which wasm >900 base pairs, was then cloned in a pGEM T-vector (Promega), amplified, and sequenced. This sequence was verified by alignment with homologous sequences from GenBank using MacVector 6.5.3 (Oxford Molecular).

5'/3' Rapid Amplification of cDNA Ends (RACE) PCR. 5'/3' RACE PCR was conducted to complete the cDNA clone of the >900 base pairs RT-PCR product described above. 1 µg mRNA was used with the 5'/3' RACE Kit (Roche Cat. No. 1-734-792), and the manufacturer's protocol was followed. Three specific primers were designed from the original RT-PCR isolated fragment and used in 5'RACE: one for first strand cDNA synthesis (SP1=GTTCACGTCGGGTGTGTTGGGCAGC) (SEQ ID NO:3), one for dA-tailed cDNA amplification (SP2=TGGTAGGTGAACAGACGGCC) (SEQ ID NO:4), and one for nesting PCR (SP3=CCCGGTCGCAGAACTCGAAA) (SEQ ID NO:5). A final primer was used for the 3' RACE reaction (SP4=ATCTACACCCTGGAGGAAGG) (SEQ ID NO:6). All PCR products were analyzed on a 1% agarose gel. PCR products that appeared to be of appropriate size were subcloned into pGEM-T vector (Promega) and sequenced as described above.

Isolation and identification of the yellow pigment associated with escapin. Purified escapin was heated at 70° C. for 15 min followed by centrifugation at 25,000×g for 20 min to separate the pigment from the protein. Yellow pigment in the supernatant was purified by HPLC according to Light et al. (1980), using a Beckman system equipped with a 168 photodiode array set at 200-600 nm with a Phenomenex luna C18 (0.46×250 mm) column. Isocratic reversed phase chromatography was performed using 5 mM ammonium acetate and 20% methanol in water as a mobile phase with a flow rate of 1 ml/min. Retention times of a FAD standard (Sigma) and the yellow pigment were compared by co-injection. ESI-TOF mass spectrometry was performed using an Applied Biosystems QSTAR XL and run in positive ion mode. ESI samples were injected into a flow of 50/50 water/acetonitrile containing 0.2% formic acid. NMR spectra were acquired on a 500 MHz Bruker Avance NMR equipped with a triple resonance cryoprobe. 1 μM of FAD standard was purified using the same method as for the yellow pigment. Spectra were recorded in $D_2O$ at 309 K. Spectra for the FAD standard were obtained under identical conditions except the experimental time. Proton assignments for the FAD standard were based on established 2D NMR methods (COSY, ROESY). The amount of FAD in the supernatant of heated protein was calculated based on an extinction coefficient value, $\epsilon_{450}$, for FAD of 11.3 $mM^{-1}$ $cm^{-1}$.

Detection of glycosylation of escapin. GelCode Glycoprotein Staining Kit (Pierce Biotechnology) was used to determine the carbohydrate component of escapin. 5 μg of escapin, bovine serum albumen (a negative control, since it lacks glycosylation), and various concentrations of horseradish peroxidase (a positive control and standard, since it is 15% carbohydrate by weight) were analyzed by SDS-PAGE followed by staining for carbohydrates according to the manufacturer's protocol, as well as by Coomassie blue labeling of proteins.

L-Amino acid oxidase (LAAO) assay. LAAO activity of escapin was determined by an enzyme-coupled assay (e.g. MacHeroux et al., 2001). Purified escapin in 50 mM PPB and 150 mM KCl was added to a 100-μl reaction mixture containing 0.1 M Tris-HCl pH 7.6, 10 μg horseradish peroxidase, 0.2 mM o-dianisidine, and indicated concentration of various L-amino acids. Reactions were performed at room temperature from 1-60 min; the activity was monitored at O.D. 436 nm and the increase in absorbance was transformed into molar concentration of end product based on $\epsilon$ of o-dianisidine=$8.31\times10^3$/M per cm. The $K_m$ and $V_{max}$ values were determined by Lineweaver-Burk plot.

Bacterial expression of the precursor of escapin. Primers were designed to amplify the whole coding sequence so that escapin could be over-expressed in E. coli. The 5' primer included a BamHI restriction site to allow in-frame insertion into the amplification and expression vectors (5'GGATCCCATGTCGTCTGCTTTCCTTC3') (SEQ ID NO:7). The 3' end included an extra HindIII restriction site (5'AAGCTTGAGGAAGTAGTCGTTGATGA3') (SEQ ID NO:8). PCR was conducted using Expand High Fidelity PCR System (Roche). The resultant whole gene fragment of expected size was cloned into pGEM-T vector (Promega), and the plasmids were amplified. The plasmids were then cut with BamHI and HindIII, and the gene was subcloned into the pET-20b expression vector (Novagen) using the same enzymes. The sequence was confirmed by DNA sequencing using an ABI sequencer at GSU Core facility. For overexpression, the plasmid was transformed into E. coli strain BL21 (λDE3). Twenty-six liters of these cells were grown in LB media in a Pilot Plant fermentor (New Brunswick Scientific) at 37° C. until reaching an O.D. 600 nm of 0.5, at which point they were induced with 0.5 mM IPTG for 2 hr. The cells were harvested, concentrated by centrifugation (5,000×g at 4° C.); a portion was resuspended in 0.1 M phosphate buffer containing 1 mM PMSF protease inhibitor, and broken on a French pressure cell (Sim-Aminco) at 16,000 psi. The resultant mixture was centrifuged at 127,000×g for 1 hr in a Beckman Coulter Optima XL-100K ultracentrifuge. SDS-PAGE was used to identify the location of escapin which formed an inclusion body and was found in the pellet. The inclusion body was first dissolved in denaturing buffer (8 M urea, 20 mM PPB buffer pH. 7.2), and the supernatant was loaded onto an anion exchange column, Mono Q 10/10 (Pharmacia) using 8 M urea, 20 mM PPB pH 7.2 and 1 mM DTT (A buffer) and the same buffer plus 1 M NaCl (B buffer) to elute escapin. Escapin was again identified by size using SDS-PAGE, and the resultant band was analyzed for MALDI-TOF MS (Emory University School of Medicine Microchemical and Proteomics Facility, http://corelabs.emory.edu/home.cfm#mcf) to verify the identity of the protein as escapin. Soluble escapin precursor could be obtained when protein was induced at lower temperature (20° C.) for 5-18 hr and tested for antimicrobial activities.

Antiserum preparation. An anti-serum against escapin was obtained by injecting rabbits with denatured recombinant escapin purified from the E. coli expression extracts. The first injection was conducted using 1:1 mixed escapin and Freund's Complete Adjuvant (DIFCO) followed by 4-5 injections using Freund's Incomplete Adjuvant (DIFCO).

Expression of escapin without signal peptide in E. coli. Similar methods as described above were used to amplify and clone escapin in E. coli. The escapin gene without signal peptide was subcloned to NdeI and HindIII sites of pET 29a vector (Novagen). Plasmid was then transformed into BL21 (λDE3) strain, and proteins were induced by 0.5 mM IPTG at O.D. 600 nm of 0.8, followed by incubation at 20° C. for 5-18 hr.

Ink Protein Concentration. In pilot studies, the purple pigment in pure ink interfered with spectrophotometric readings used in the standard Bradford assay of protein concentration. For this reason, ink protein content was approximated by SDS-PAGE of ink samples. Three known quantities of BSA were used to calibrate a Calibrated Imaging Densitometer GS-710 (Biorad). Protein concentration measurements established ecologically acceptable levels of escapin for the sea anemone tentacle assay.

Antimicrobial assay. Assays of antibacterial activity were performed in either liquid media or solid media on Petri dish plates with 1.5% agar. E. coli was cultured in either Luria-Bertani (LB) or M9 glucose media. Other bacteria were cultured in LB medium, except for Streptococcus pyogenes, which was cultured in Todd Hewitt broth. In assays using solid media on plates, various bacteria species and strains were plated as the lawn of ca. $1-2\times10^8$ cells, and antimicrobial activity was examined by spotting 1 μl of escapin onto the plate, incubating overnight at 37° C. or room temperature, and assaying for the presence of a clear zone around the spot. In assays using liquid media, antibacterial activity was determined by co-incubating bacteria with escapin, followed by turbidity measurement at O.D. 600 nm or by counting the number of viable colonies after growing serial diluted cultures on LB agar plates. Anti-fungal assays were carried out using solid Sabouraud Dextrose medium. Anti-yeast assays were run using YEPD solid medium (1% yeast extract, 2% peptone, 2% dextrose).

Microbial species and strains. Eleven species or strains of microbes were examined: Gram-negative bacteria Escherichia coli (MC4100), Pseudomonas aeruginosa (PAO1), and Salmonella typhimurium (AA140), Vibrio harveyi BB170, Gram-positive bacteria Bacillus subtilis (2 strains, 168 and WB600), Streptococcus pyogenes (NZ131), and Staphylococcus aureus (6835); yeast Candida krusei and Saccharomyces cerevisiae (BY4761); and fungus Cladosporium sp.

Assay of antimicrobial shelf-life at room temperature. Long-term stability of the antimicrobial activity of escapin was evaluated to aid in determining its potential as a practical antimicrobial agent. 250 μg/ml of escapin in buffer containing 50 mM buffer (pH 8.0) and 150 mM KCl was diluted at 1:1 ratio in the same buffer with or without 100% glycerol, separated into aliquots, and stored at room temperature for time intervals more than 5 months. Control escapin was kept frozen at −80° C. until used. The shelf-life of escapin was determined by 2-fold serial dilutions on a solid LB medium antibacterial assay using *E. coli* or *B. subtilis*.

RESULTS

Proteins in the Ink of *Aplysia californica*

SDS-PAGE was used to identify dominant bands that might correspond to those already known from different species of sea hares. The results showed that indeed there was one dominant protein of about 60 kDa (FIG. 1). This was in the size range of proteins reported in the ink of other sea hares (Yamazaki 1993).

In *Aplysia californica*, the ink gland contains mostly purple vesicles but also a large population of amber-colored vesicles (Johnson and Willows, 1999). The function of these amber colored vesicles had not been determined. Microdissection was used to remove intact purple and amber vesicles, and pure vesicles were tested on SDS-PAGE. The protein appeared only in the amber vesicles (FIG. 1). TEM micrographs taken at about the same time showed what looked like protein crystals in the amber vesicles of *A. californica*.

Figure 2A:
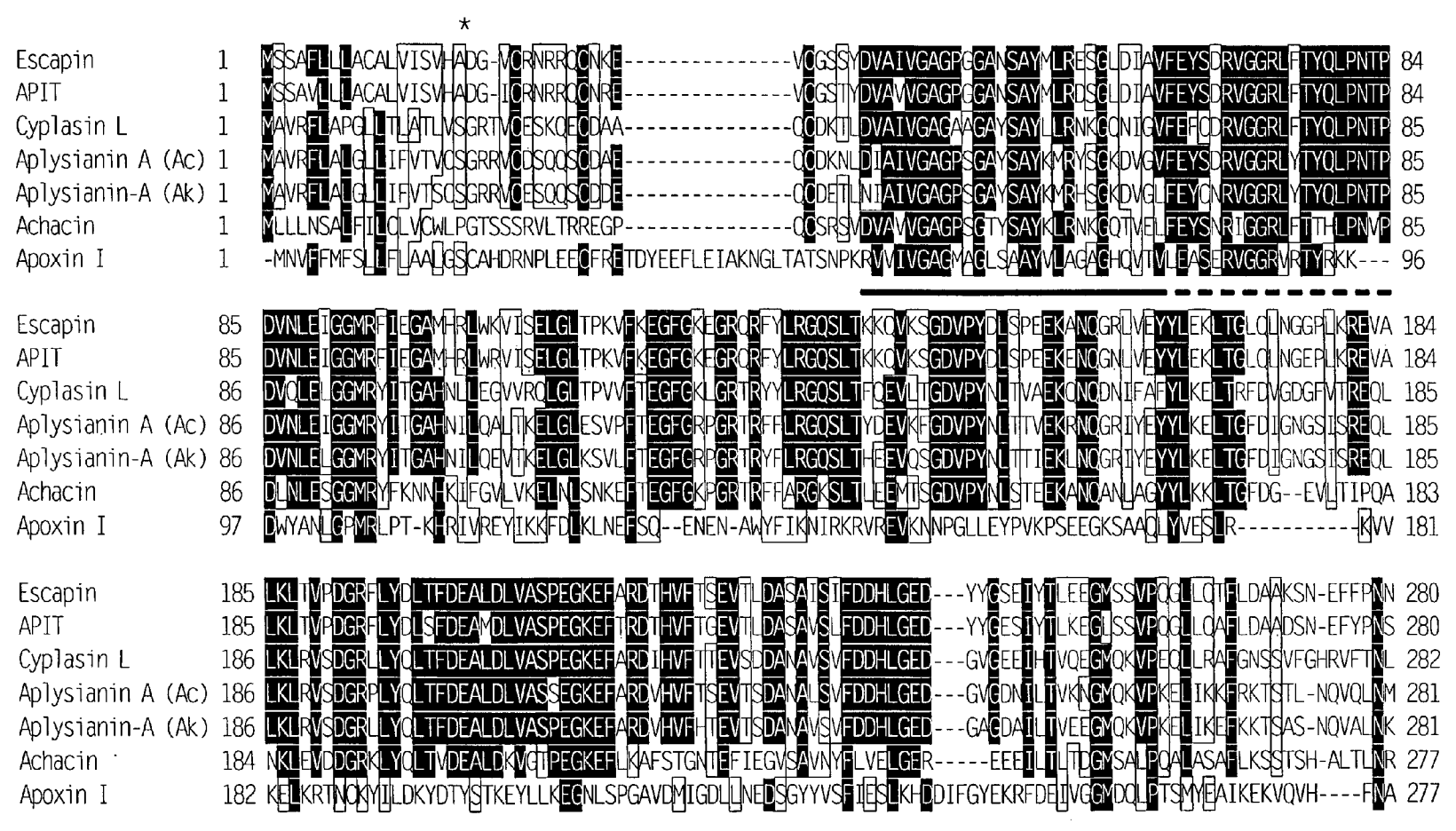
Figure 2B:
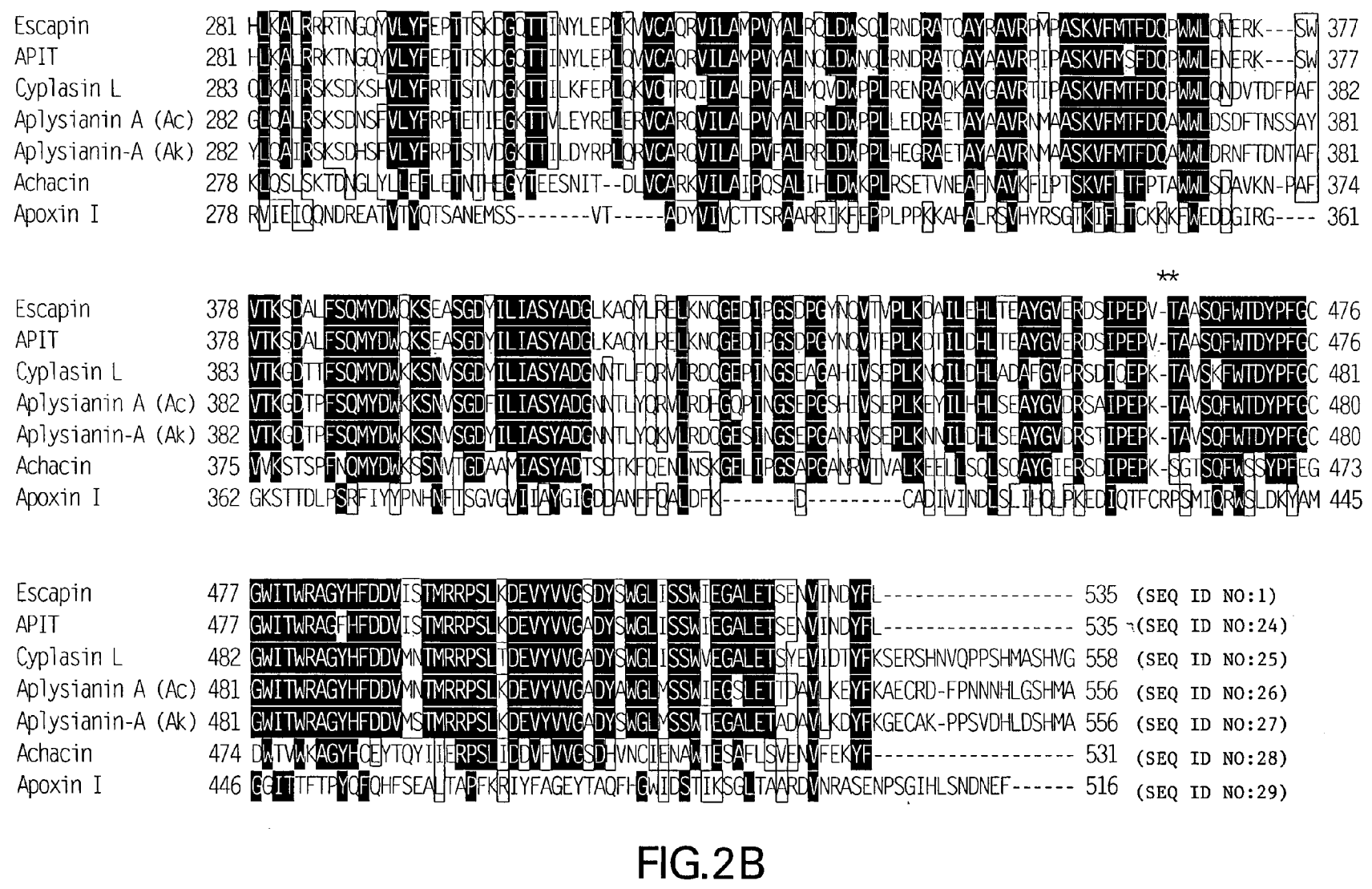

The cDNA of escapin was 1879 bp in length (GenBank accession number AY615888) and had an open reading frame encoding for 535 amino acid residues (FIG. 2). Based on the deduced amino acid sequence, a signal peptide cleavage site between 18 and 19 amino acid residues was predicted by SignalIP. This was verified by N-terminal amino acid sequencing of native escapin isolated from sea hare ink.

A BLAST search (FIG. 2) found that escapin shared identity with a number of L-amino acid oxidase (LAAO) flavoproteins. Escapin had highest identity (93%) with APIT, a protein from the purple ink secretion of the sea hare *Aplysia punctata* (Accession #442281, 442282, 4422883). Escapin shared 61% identity with cyplasin L (Accession #AJ304802), likely isolated from an ink-opaline secretion of *A. punctata*. Escapin shared 61% and 60% identity with aplysianin A precursor protein isolated from albumen glands of *A. kurodai* (Accession #D83255) and *A. californica* (Accession #AY161041) respectively. Escapin also had 48% identity with achacin precursor, an antibacterial protein isolated from a land snail *Achatina fulica* (Accession #X64584). It also showed 21% identity with other L-amino acid oxidases from various species, including apoxin I from the venom gland of the pit viper *Crotalus atrox* (Accession #AF093248).

The alignment results indicate that the two characteristic sequence motifs of flavoproteins are well conserved among these proteins (FIG. 2). Glycosylation is commonly observed among LAAOs and is reported to be critical for the enzyme's activity (Ehara et al., 2002; Ogawa et al., 1999; Torii et al., 2000). However, only one possible N-glycosylation site (Thr 463) was predicted for escapin by the analytical program NetOGlyc. The level of glycosylation of purified escapin was directly examined using a glycoprotein-staining method. Escapin contains no detectable carbohydrates, with the resolution of the assay being ca. 1.5% carbohydrate by weight. Therefore, escapin appears to be minimally glycosylated if at all, probably no more than one N-glycosylation site. Further, no evidence was found that the glycosylation is essential to escapin's antimicrobial activity.

Escapin is a Member of Flavoprotein Family.

Figure 4A:
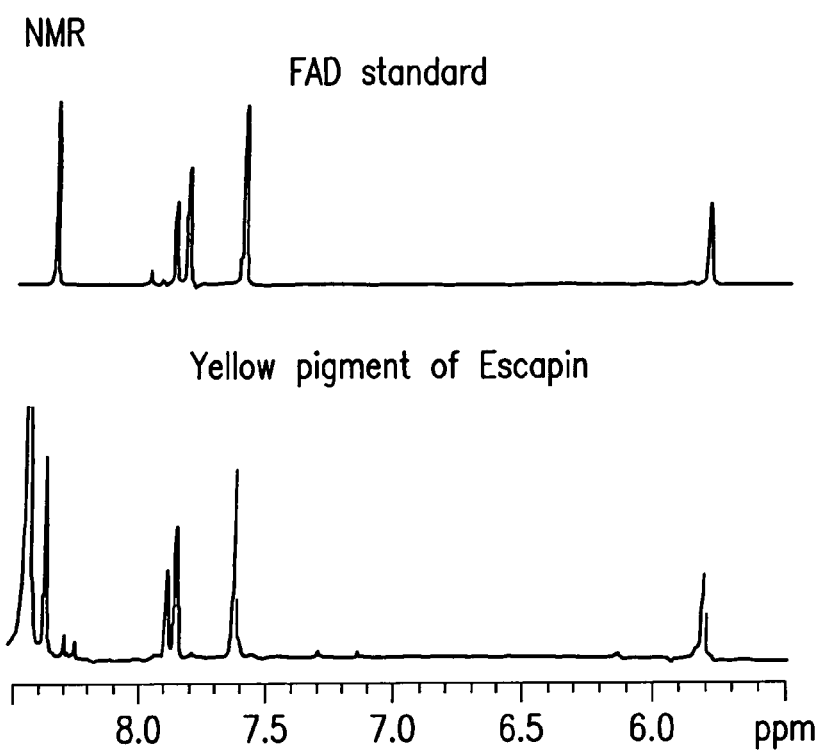
FIG. 4 shows the yellow pigment associated with escapin is FAD. (A) Aromatic region of 1H NMR spectrum for FAD standard and the yellow pigment from escapin, showing identical signals. (B) Positive ion ESI-TOF mass spectrum of the yellow pigment from escapin.
Figure 4B:
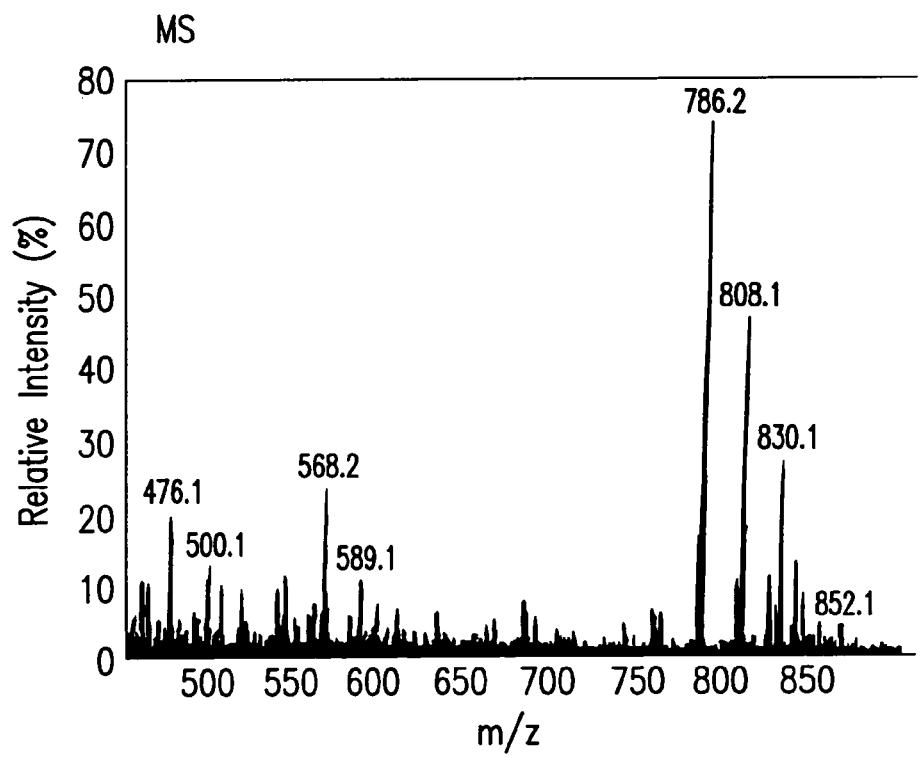

Amino acid sequence analysis suggested that escapin is a member of the flavoprotein family, and contains "GG" (RxGGRxxS/T) and βαβdinucleotide-binding (DMB) motifs. Purified homogeneous escapin was bright yellow, and it was assumed that this yellow pigment was the flavin. Since flavin adenine dinucleotide (FAD) is the typical flavin co-factor for this protein family, NMR, ESI-TOF mass spectroscopy, and HPLC were used to search for the presence of FAD. The aromatic and aromatic regions of the $^1$H NMR spectrum of the yellow pigment isolated from escapin showed essentially identical resonances as the FAD standard, although the spectrum of the yellow pigment contained signals of impurity at 8.45 ppm (FIG. 4A). Similar features were also obtained for the aliphatic region of the FAD standard and the yellow pigment. Particularly noteworthy is the fact that two of the aromatic protons (7.8 ppm) that have long T1 relaxation times in FAD are also observed for the pigment. A high-resolution ESI-TOF mass spectrum of purified yellow pigment from escapin showed a peak with an m/z value of 786.1641 (FIG. 4B); this corresponds to the molecular formula $C_{27}H_{34}N_9O_{15}P_2$, which was designated as a $(M+H)^+$ ion of FAD. ESI-TOF mass spectrum of the yellow pigment also showed peaks at m/z of 808.1 and 830.1, which correspond to the $(M+Na)^+$ and $(M-2H+Na)^+$ ions of FAD (FIG. 4B). In this spectrum, signals below 400 m/z were due to solvents, and signals of 400-600 m/z were not identified. Ions corresponding to another flavin, FMN (molecular mass=478.3), were not found. In addition, in reversed phase HPLC, the yellow pigment had the same retention time (17.6 min) as FAD, and co-injection of the yellow pigment and FAD showed only one peak. UV-visible absorbance spectrum of the peak of the yellow pigment showed absorbance at 263, 375, and 450 nm, which is characteristic for FAD. Thus, the yellow pigment released from escapin is FAD. Based on $\epsilon_{450}$ values, 17.2 nmole FAD was extracted from 16.7 nmole of purified escapin, yielding an escapin: FAD molar ratio of about 1:1.

Figure 5:
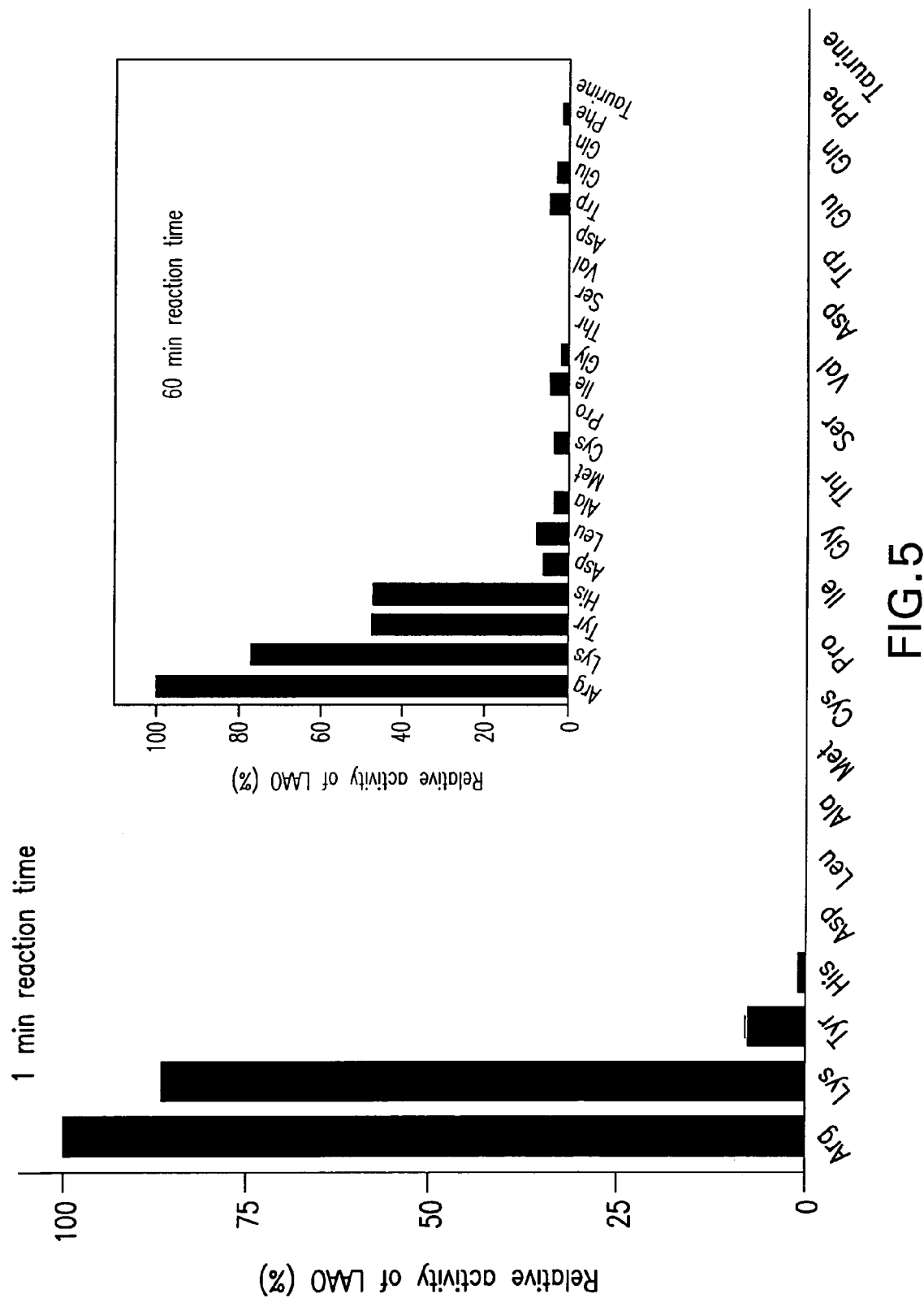
FIG. 5 shows LAAO enzyme activity of escapin and its substrate specificity. 0.6 µg escapin was incubated at 22° C. for 1 min (main figure) or 60 min (inset) in 2 mM of each L-amino acid and taurine. LAAO activity was measured at O.D. 436 nm and normalized to arginine. Values are mean±S.E.M., n=2.
Figure 7:
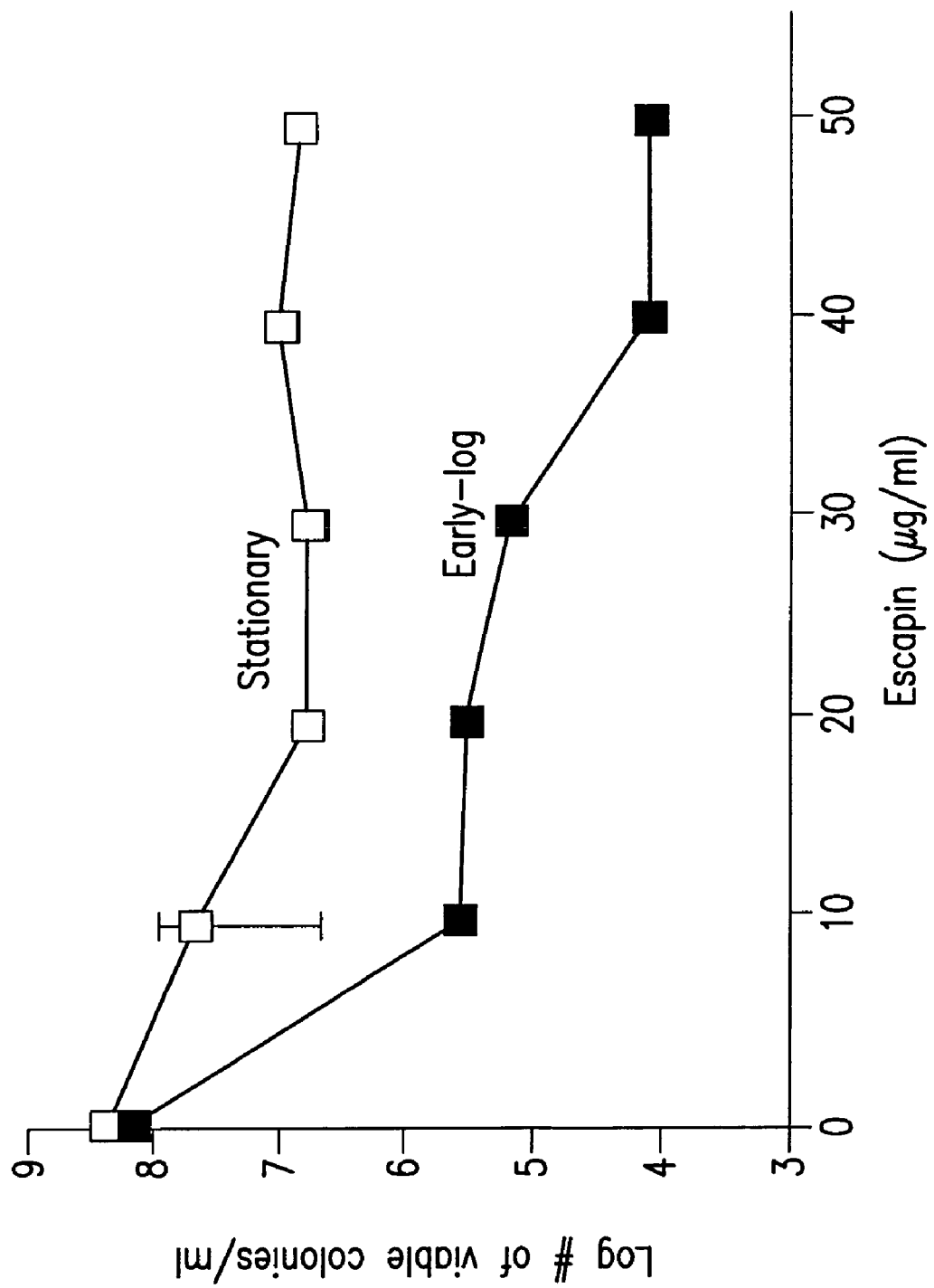
FIG. 7 shows escapin preferentially kills *E. coli* cells in their growing but not resting state. $2 \times 10^8$ cells/ml in early-log growth or stationary phase were centrifuged, and the pellet was resuspended in fresh LB medium. O.D reading was adjusted to that of early-log phase cells (=0.5). Cells were then co-incubated in escapin from 0-50 μg/ml at 37° C. for 2 hr. Cultures were then placed on LB agar plates and incubated for 18 hr, at which time the number of viable colonies was counted. Values are mean±S.E.M., n=3.

Results from an NCBI conserved domain search predicted that escapin is an L-amino acid oxidase (LAAO). To test this prediction, an enzyme-coupled oxidase assay was performed. The results confirmed the prediction, showing that amino acids serve as a substrate for escapin (FIG. 7). Unlike LAAOs from African snail and snake venom (Du and Clemetson, 2002; Ehara et al., 2002; Lu et al., 2002; MacHeroux et al., 2001; Torii et al., 1997), but similar to aplysianin A isolated from albumen gland of *Aplysia kurodai* (Jimbo et al., 2003), escapin preferentially utilized positively charged amino acids. The most effective amino acids were L-lysine and L-arginine (FIG. 5), with $K_m$ (μM) and $V_{max}$ (μM/s) values of 31 and 1.92 for lysine and 25 and 1.56 for arginine (FIG. 5, for 1 and 60 min assays). The reactions were completed within 30 sec at room temperature for lysine or arginine concentrations of 0.02-2 mM.

Antimicrobial Activity of Escapin.

Escapin inhibited the growth of several types of bacteria including Gram-negative (*Escherichia coli, Pseudomonas aeruginosa, Salmonella typhimurium, Vibrio harveyi*) and Gram-positive (*Bacillus subtilis, Streptococcus pyogenes,* and *Staphylococcus aureus*) (Table 2). *Vibrio harveyi*, a marine bacterium, was most sensitive to escapin, with a minimum inhibitory concentration of 0.25 μg/ml. *Bacillus* of both wild-type and protease-deficient strains showed the highest resistance to escapin, with minimum inhibitory concentrations of 2.5 μg/ml. Escapin also exhibited anti-fungal and anti-yeast activity, though it was less effective against them than bacteria. The minimum effective concentrations of escapin against a common pest mold *Cladosporium* sp. and a pathogenic yeast strain *Candida krusei* were 62 and 5 µg/ml respectively, which is 10-100 times higher than against *E. coli* (Table 2).

Figure 6:
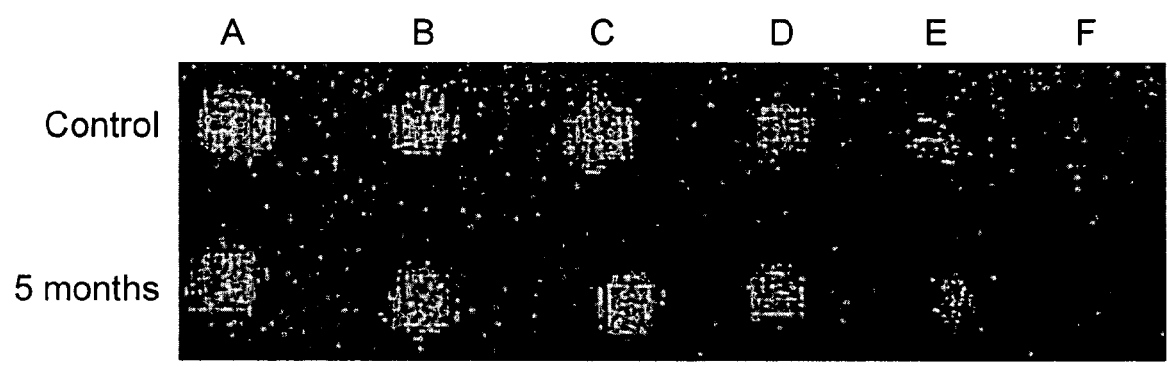
FIG. 6 shows escapin has a very long antimicrobial shelf-life at room temperature. *E. coli* cells in stationary phase were grown as a lawn on solid medium and tested for antibacterial activity against escapin in two conditions: 'control': 0 time at room temperature; '5 months': 5 months at room temperature. Escapin concentration was 125 µg/ml in column A; columns B-F represent a series of 2-fold dilutions of the proteins.

Escapin has a very long shelf-life at room temperature (FIG. 6). Escapin with or without 50% glycerol retained the same antibacterial activity over a period of more than 5 months stored at room temperature. Unlike other LAAOs found in snake venom (MacHeroux et al., 2001), escapin is also highly stable when taken through several freeze-thaw cycles.

Escapin preferentially killed cells in early-log growth phase over resting cells (FIG. 7). This shows that escapin acts on growing rather than stationary phase cells.

Figure 8:
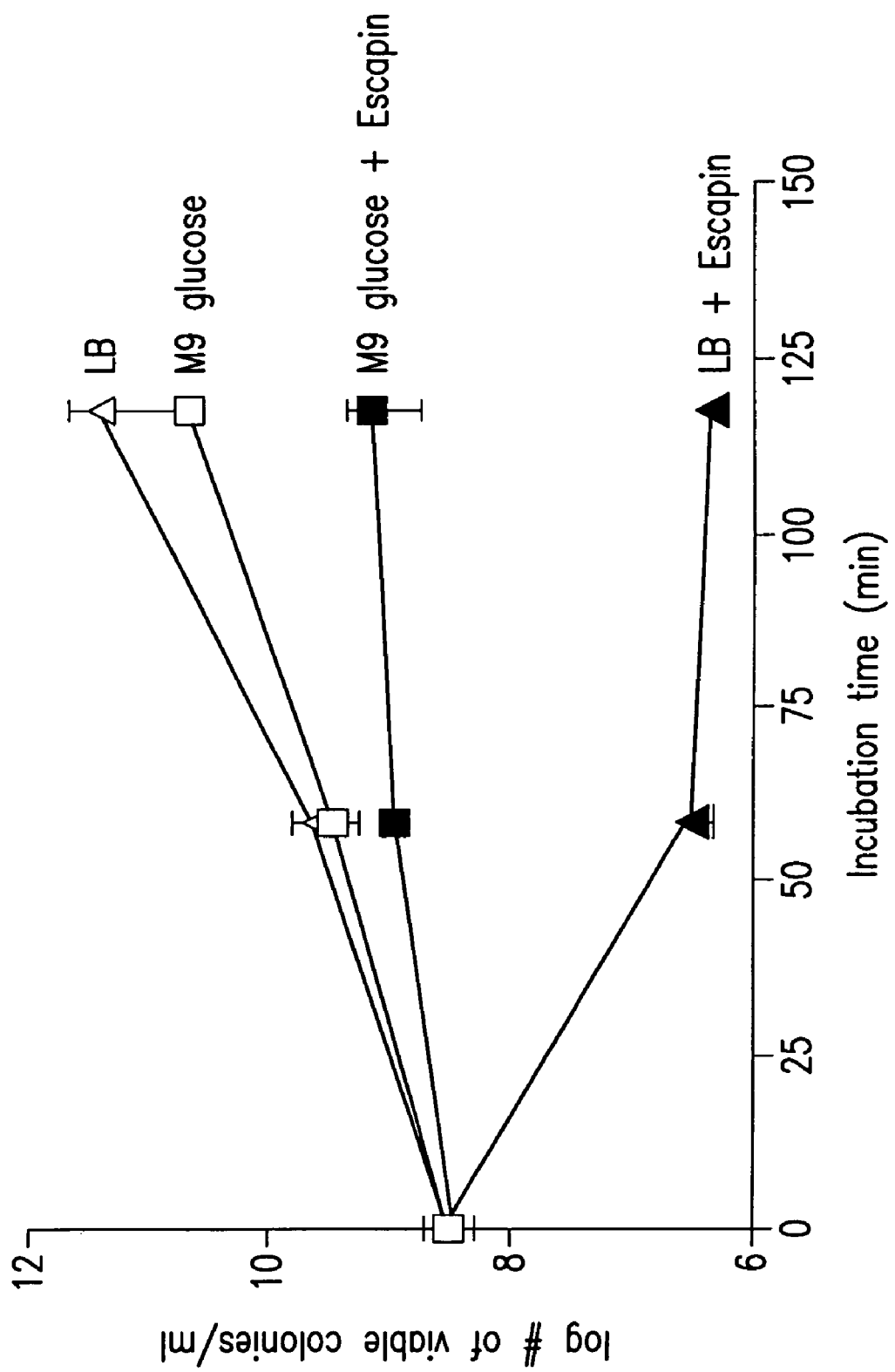
FIG. 8 shows that the type of growth medium determines whether escapin is bactericidal or bacteriostatic. $E.\ coli$ cells were grown in M9-glucose medium, then equally divided into 4 portions each containing $3\times10^8$ cells/ml. These were then incubated with (solid symbols) or without (open symbols) escapin (10 μg/ml) in M9-glucose (square) or LB (triangle) medium at 37° C. for 2 hr. Escapin in M9-glucose medium inhibits the typical increase in number of viable cells (i.e., is bacteriostatic), whereas escapin in LB medium reduces the number of viable cells (i.e., is bactericidal). Values are mean±S.E.M., n=3.
Figure 9A:
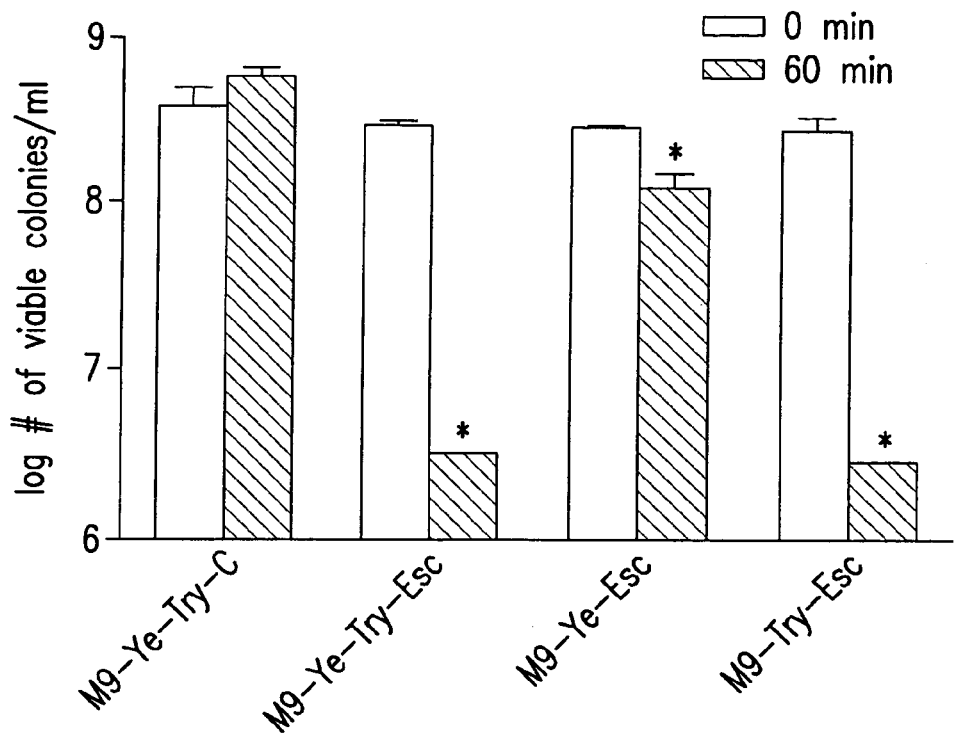
FIG. 9 shows escapin's anti-bactericidal effect on early-log growth $E.\ coli$ cells was greatest in the presence of higher concentration of lysine or Tryptone Peptone. $E.\ coli$ cells were cultured in M9-glucose medium, and 4 aliquots of $5\times10^8$ cells/ml were resuspended in different growth media in the presence of escapin (50 μg/ml) or buffer control (C). Cells were then incubated at 37° C. for 60 min. Media: (A) M9, M9-glucose; Ye, 1% yeast extract; Try, 1% Tryptone Peptone; (B) M9, M9-glucose; Lys, 50 mM L-lysine; Arg, 50 mM L-arginine; His, 50 mM L-histidine; Val, 50 mM L-valine; aa, amino acid mixture containing 20 L-amino acids each at 50 μM. In a follow-up experiment, 10 times higher concentration of Ye or aa was used, and similar results were observed. Values are mean±S.E.M., n=3. Asterisk indicates a significant reduction in the number of viable clones (P<0.05, T test).
Figure 9B:
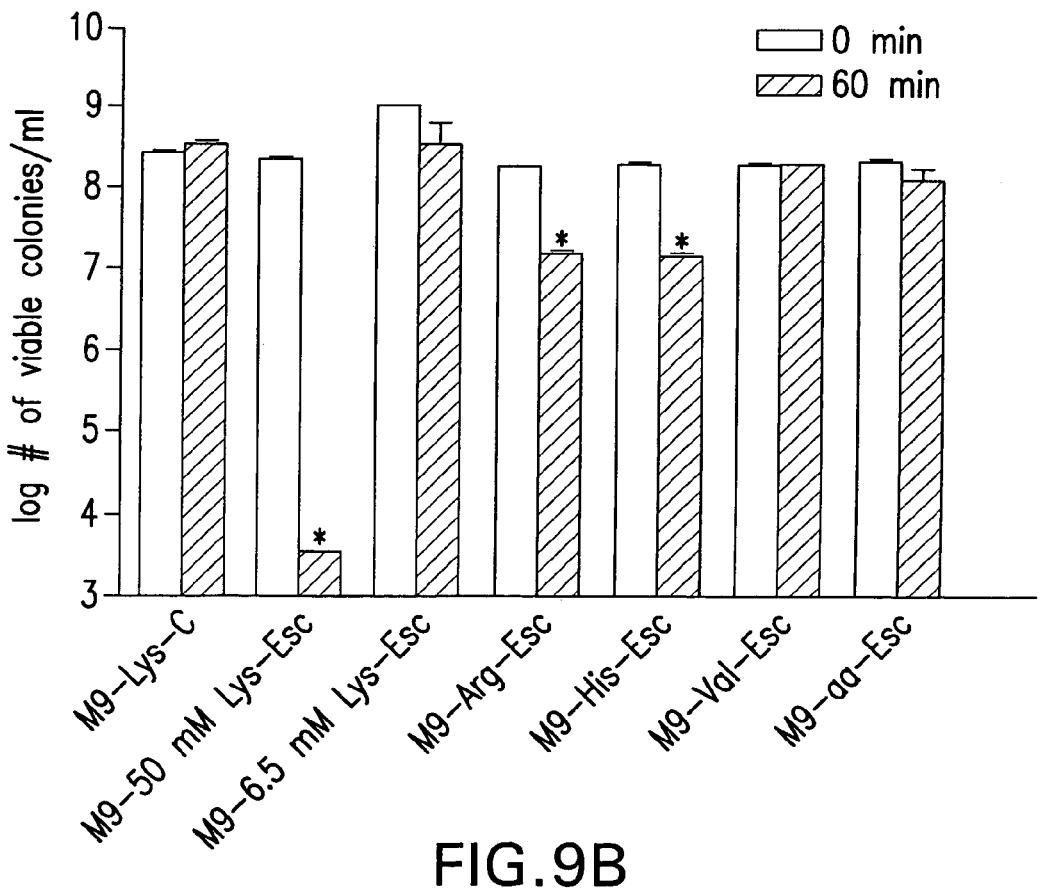
Figure 10:
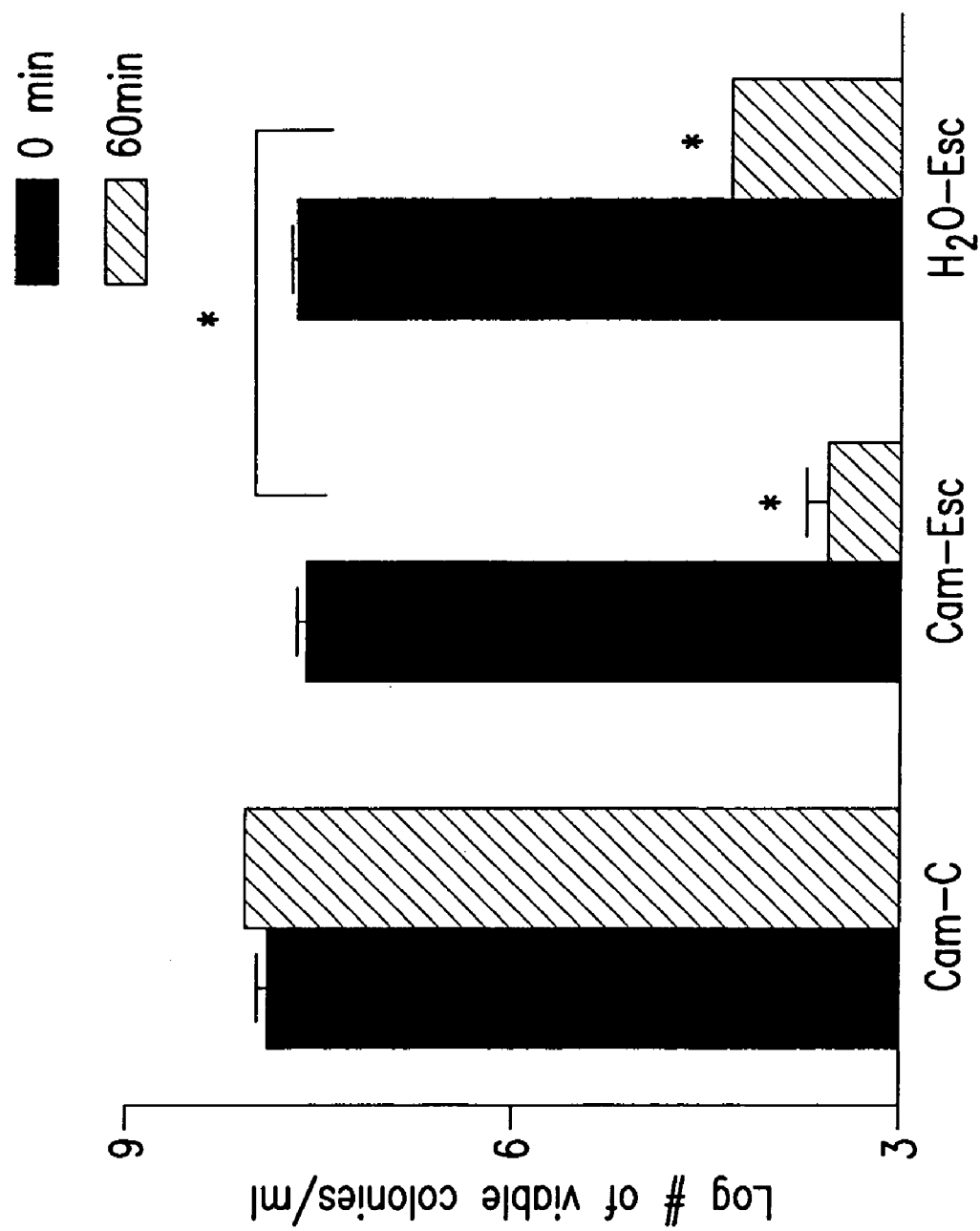
FIG. 10 shows escapin's bactericidal effect does not require protein synthesis. $2\times10^8$ $E.\ coli$ cells/ml were incubated with or without 50 μg/ml chloramphenicol (Cam), an inhibitor of protein synthesis, in the presence of 50 μg/ml escapin (Esc) or buffer control (C) in LB medium at 37° C. Values are mean±S.E.M., n=3. Asterisk indicates a significant reduction in the number of viable clones (P<0.05, T test).

The type of growth medium influences whether escapin is bacteriostatic or bactericidal against *E. coli*. In M9 glucose minimal medium, escapin was bacteriostatic, whereas in LB medium, escapin was bactericidal (FIG. 8). To understand further this effect, escapin was co-incubated with the separated components of LB, or with individual amino acids. Tryptone Peptone or a high concentration (50 mM) of lysine, but not yeast extract, other individual amino acids such as arginine, or an amino acid mixture, was as a major co-factor in escapin's bactericidal effect (FIGS. 9A, B). The bactericidal effect of escapin did not directly involve protein synthesis, since addition of chloramphenicol (a protein synthesis inhibitor) did not affect escapin's bactericidal effects in LB medium. In contrast, it enhanced the killing effect by at least one-log unit (FIG. 10).

Figure 11:
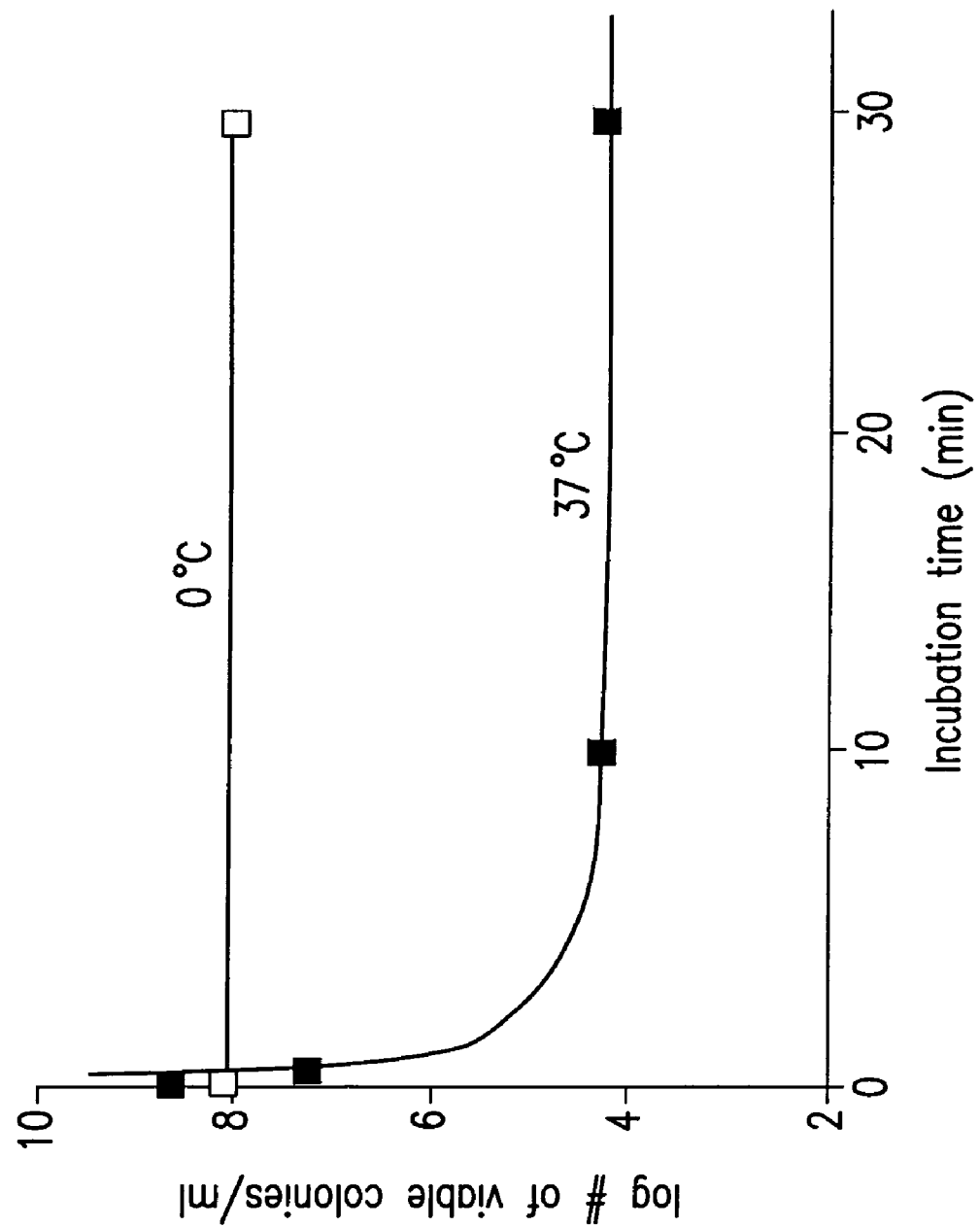
FIG. 11 shows escapin quickly kills $E.\ coli$ cells. $4\times10^8$ cells/ml in early-log phase were incubated with 10 μg/ml escapin in LB growth medium at 37° C. or 0° C., and cell viability was measured at indicated time intervals by counting the number of colonies. Values are mean±S.E.M., n=3.

Killing occurred rapidly—within 10 min—and was maintained for up to 2 hr when cells were incubated at 37° C. but not 0° C. (FIG. 11). To verify that the absence of a bactericidal effect of escapin at 0° C. is due to the cells being in a resting state rather than the low temperature inactivating escapin, the oxidase activity of escapin at 0° C. was examined. Escapin is active at 0° C. but with a lower rate than at 22° C. Thus, escapin's ability to kill *E. coli* requires metabolic activity but not protein synthesis by the bacteria.

Antibacterial Effect of Escapin is Mediated at Least Partially by Hydrogen Peroxide Production.

Figure 12:
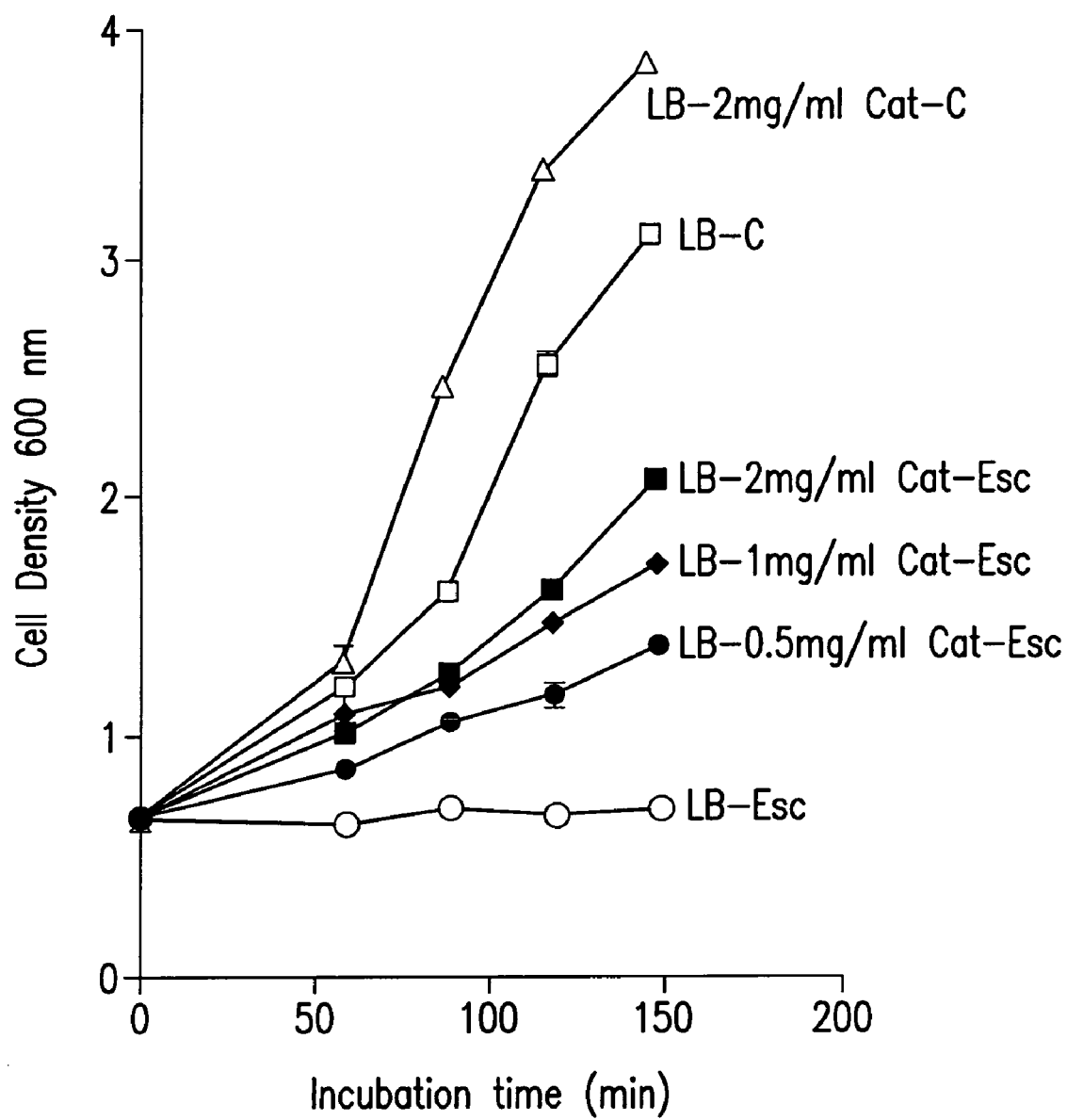
FIG. 12 shows the antibacterial effect of escapin is at least partially due to production of hydrogen peroxide. $E.\ coli$ cells were incubated in LB medium at 37° C. with 10 μg/ml escapin or without escapin (buffer (C) added instead), and with or without 0.4-1.6 mg catalase (Cat). Cell density was measured at an O.D. of 600 nm at the indicated incubation times.

Previous reports (Butzke et al., 2004; Suhr and Kim, 1996; Torii et al., 1997, 2000) have indicated that the antibacterial and cytotoxic activities of numerous LAAOs are mediated through hydrogen peroxide ($H_2O_2$) production. Therefore the contribution of $H_2O_2$ production to the antibacterial activity of escapin using the $H_2O_2$ scavenger catalase was examined. Catalase inhibited escapin's antibacterial activity in a concentration-dependent manner (FIG. 12). At the highest catalase concentration tested (catalase:escapin ratio of 17:1; note that catalase functions as a tetramer), there was 55% inhibition of escapin's antibacterial activity. In addition, cell density remained constant over a 2-hr inhibition period, suggesting that escapin exerts its bactericidal effects by mechanisms other than lysis (FIG. 12). Similar results were observed in FIG. 10B, that lysine but not arginine serves as a major co-factor in escapin's bactericidal effect even though enzymatic production of $H_2O_2$ is higher for arginine than for lysine. Together, $H_2O_2$ production is not the major mechanism but is at least partially responsible for bactericidal effects of escapin.

Purification of the Ink Protein

To determine if the dominant protein was indeed responsible for the antibacterial activity as well as the response of sea anemones, the protein was isolated and purified from the crude ink secretion. Early attempts to separate the protein from the algal pigments in the ink, including salting-out the protein with ammonium sulfate and spin filtration through molecular weight cut-off membranes, failed. The algal pigments, though only a few hundred Daltons in size, seemed to show a strong affinity for the protein and were not easily separated.

A published 25-step separation protocol (Melo et al., 2000) that had been used for the protein in the ink of *A. dactylomela* was modified, reducing the number of steps to five using two Fast Protein Liquid Chromatography (FPLC) columns. Pure ink, collected as described above, was loaded directly onto either a Hi-load Superdex 200 16/60 (Pharmacia) or a Sephacryl 300 HR column made in the lab for size separation. This larger Sephacryl column could support the loading of 13 ml of ink in a single run. The proteins eluted before most of the pigments and thus permitted separation of the two. The fractions were analyzed both with SDS-PAGE and the antibacterial assay to determine which peaks contained the protein. Once the appropriate peak from the FPLC had been identified, it could be isolated in all subsequent runs. The active fractions were mixed together and concentrated using Biomax 5K Centrifugal Filter Devices (Millipore) and then re-diluted in buffer and loaded onto the second column, the Mono S 5/5 (Pharmacia). Mono S is a cation exchange column that has a high affinity for proteins with low pKa values. The pKa for *A. californica* ink protein was estimated to be 5.08 and thus tightly bound to the column. This produced a clean peak on the FPLC and a clean single band on SDS-PAGE. Antibacterial assays confirmed that this was indeed the active protein in *A. californica* ink. After purification, the native protein appeared to be pigmented. It had the same amber color of the vesicles from which it was located in the ink gland.

Gene Cloning

Purification requires a large number of animals because one adult *A. californica* (~200 g) produces about 0.5-0.7 ml of ink. Ink protein isolated from *A. californica* ink was sent to Dr. John Leszyk at the University of Massachusetts for sequencing. One internal sequence appeared to be novel (ESGLDIAVFEYSDR) (SEQ ID NO:9), but another internal sequence of 15 amino acids (VFMTFDQPWWLQNER) (SEQ ID NO:10) matched exactly the first 13 of an internal sequence of cyplasin L and S that were submitted to NCBI in December 2000 (Accession numbers: CAC19362 and AJ304801). The cyplasins, isolated from a European species of sea hare, *Aplysia punctata*, were reported to be antibacterial and cytolytic. Six primers for RT-PCR from the Cyplasin L sequence, including four 5' primers: (1) TTCGAGTTCTGCGACCGGGT (SEQ ID NO:11), (2) TCATGSAAGTGGACTGGCCC (SEQ ID NO:12), (3) TGACCTTTGACCAGCCTTGG (SEQ ID NO:13), (4) AGACGGTGGTTGCACGTTGT (SEQ ID NO:14), and two 3' primers: (1) CCAAGGCTGGTCAAAGGTCA (SEQ ID NO:15) and (2) AGTCCCCAGAAACGTTGGAC (SEQ ID NO:16). Two degenerate 5' primers from the *A. californica* ink protein sequence were also designed: CGIAACTCGIGACTCAG (SEQ ID NO:17) and GAGATCIGGICTIGACTATACTGC (SEQ ID NO:18). As used herein in the nucleotide sequences, "I" and "N" represent a degenerative nucleotide; that is, "I" and "N" can be an "A," a "T," a "C," or a "G." The RT-PCR product after cloning, amplification, and sequencing produced one fragment of 955 base pairs that was aligned with cyplasin L. 5'/3' Rapid Amplification of cDNA Ends (RACE) PCR produced 5' and 3' fragments that completed the gene.

Expression of Bioactive Recombinant Escapin in *E.coli* System.

Figure 13A:
FIG. 13 shows recombinant escapin and its antibacterial activity. (A) Western blots demonstrating successful expression of recombinant escapin. (B) Anti-bacterial activity of wild-type and recombinant escapin. $E.\ coli$ cells in stationary phase were grown as a lawn on solid medium and tested against wild-type and recombinant escapin. Escapin concentration was 60 μg/ml in Column A, and recombinant escapin in column A was adjusted to approximately the same level based on Western blots. Columns B-D represent a series of 2-fold dilutions of the proteins. wEsc: wild-type escapin purified from ink. r-proEsc: recombinant escapin, with 18 amino acid signal peptide, in $E.\ coli$ cell lysate. rEsc: recombinant in $E.\ coli$ cell lysate, escapin without signal sequence (i.e. lacking 18 amino acids at N-terminal). M: molecular weight markers.
Figure 13B:
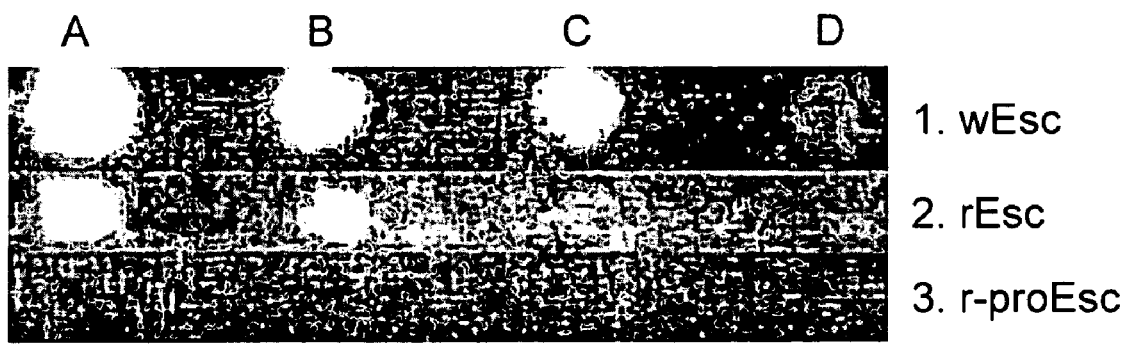

Because escapin is minimally glycosylated, the possibility of using prokaryotic systems to produce bioactive escapin was studied, using two recombinant sequences: full length escapin (rEsc) and escapin precursor (r-proEsc). r-proEsc is rEsc plus the 18-amino acid signal peptide and 29 additional amino acids from the vector added to the N-terminus (SEQ ID NO:23). This construction is the only one that can be stably expressed because the clone without the extra amino acids from the vector in the signal peptide results in a truncated protein. The r-proEsc and rEsc genes were cloned into pET20b and pET 29a, respectively, and both were transformed into BL21 (λDE3) strain and expressed in *E. coli*. Soluble recombinant proteins with lower expression levels were obtained when proteins were induced at lower temperature (20° C.) and at a shorter time. In contrast, inclusion bodies with higher expression levels were obtained under induction at 37° C. Thus, denatured recombinant escapin precursor (r-proEsc) was used for production of antiserum. Expressed r-proEsc and rEsc were confirmed by Western blot to be present in the *E. coli* cell lysate (FIG. 13A). As expected, r-proEsc containing a signal peptide showed the highest molecular weight. However, rEsc ran slightly lower on the gel than did native escapin. Antibacterial activity of the recombinant proteins was determined using plate assays with lawns of cells grown on solid LB medium. For the Gram-negative *E. coli*, rEsc had antibacterial activity (FIG. 13B), although its activity was 3-4 times less than that of wild-type escapin (wEsc). This observation shows that glycosylation is not essential for antimicrobial activity. r-proEsc had no activity on *E. coli*. Similar results were obtained with the Gram-positive bacterium *Staphylococcus aureus*.

Example 2

Method for Purification of Escapin from the Ink of *Aplysia californica*

Pure ink, collected from dissected ink glands that were gently squeezed into a Petri dish or from manipulating a live sea hare, was loaded directly onto either a Hi-load Superdex 200 16/60 (Pharmacia) or a Sephacryl 300 HR column made in the lab, both for size separation, using 50 mM phosphate buffer pH 7.2 containing 150 mM NaCl and 1 mM EDTA. This large Sephacryl column could support the loading of 13 ml of ink in a single run. The proteins eluted before most of the ink pigments and thus permitted separation of the two. The fractions were analyzed both with SDS-PAGE and an antibacterial assay to determine which peaks contained the protein. Once the appropriate peak from the FPLC had been identified, it could be isolated in all subsequent runs.

The active fractions from the Sephacryl column were mixed together and concentrated using Biomax 5K Centrifugal Filter Devices (Millipore) and then re-diluted in buffer and loaded onto the second column, the Mono S 5/5 (Pharmacia). Mono S is a cation exchange column that has a high affinity for proteins with low pKa values. The pKa for Escapin was estimated to be 5.08 and thus bound tightly to the column. This produced a clean peak on the FPLC by NaCl gradient elution of buffer B, which containing 25 mM phosphate buffer pH 6.4 and 1 M NaCl, from buffer A, which contained the same buffer without the NaCl. Additionally, a clean single band was observed on SDS-PAGE. Antibacterial assays confirmed that this was the active protein in *A. californica* ink. After purification, escapin appeared to be pigmented. It had the same amber color of the vesicles from which it was located in the ink gland.

Antimicrobial Activity of Escapin

Escapin has a broad spectrum of anti-microbial activities, including inhibition of growth of Gram-negative and Gram-positive bacteria, yeast, fungi, and cyanobacteria (blue-green algae). See Table 2.

Escapin is Antibacterial.
Antibacterial effects of escapin have been demonstrated on the Gram-negative bacteria *Escherichia coli*, *Pseudomonas aeruginosa*, and *Salmonella typhimurium*, and *Vibrio harveyi*; and the Gram-positive bacteria *Bacillus subtilis*, *Streptococcus pyogenes*, and *Staphylococcus aureus*. See Table 2. In all cases, escapin inhibited the growth of bacteria on agar plates.
It inhibits growth of *E. coli* quickly, killing them without lysis.
The active concentration of antibacterial activity of Escapin is as low as 0.06-0.08 mg/ml.
Escapin is very stable.
It retains its inhibitory activity for more than 3-6 months at room temperature.
It retains its activity after treatment with Pronase, which is a mixture of proteases that digest Escapin into small fragments.
It is inhibited by catalase (an anti-oxidase).

Escapin is Antifungal.
*Cladosporium* is a fungus (pest mold) that is a common allergen that frequently grows on the surface of fiberglass duct liners in the interior of air supply ducts. It is also known to grow on paint, textiles, and other surfaces that may become moist. *Cladosporium* can cause mycosis and extrinsic asthma (immediate-type hypersensitivity: type I), acute symptoms of which include edema and bronchospasms and can lead to pulmonary emphysema.
Escapin inhibits growth of *Cladosporium* at a concentration of 1 mg/ml.
This activity is stable. At 1 mg/ml, escapin inhibits growth of *Cladosporium* for more than 10 months at 4° C.
This activity was inhibited by treatment with the enzyme catalase.
This activity was not inhibited by pronase.

Escapin is Anti-cyanobacterial.
Cyanobacteria are one of several common marine and freshwater biofouling organisms.
Escapin inhibits growth of the cyanobacterium *Synechocystis* at a concentration of 2.5 mg/ml.
Escapin is stable. Escapin at 2.5 mg/ml inhibits for more than 10 months at 4° C.

Glycosylation of Escapin

Three techniques suggest that escapin has no or at most very minor glycosylation. Thus, bacteria that typically do not add glycosylation sites to the proteins they express can be an adequate cell expression system for escapin.

UGA Complex Carbohydrate Facility: The Complex Carbohydrate Facility at UGA attempted to identify glycoproteins in purified Escapin. This facility uses enzymatic methods for de-glycosylation, followed by biochemical determination of carbohydrate components. After de-glycosylation, the carbon fraction showed yellow color and the protein fraction retained light yellow color. Both fractions were tested for antibacterial assay, and results showed that protein fraction retained antibacterial activity but not the carbon fraction. From bioinformatic computation prediction, there is only one possible N-glycosylation site and there are multiple O-glycosylation sites of Escapin.

Detection of Glycosylated Proteins by GelCode Glycoprotein Staining Kit (Pierce Biotechnology): Five micrograms of purified Escapin were analyzed by SDS-PAGE and stained with GelCode Glycoprotein staining kit to verify the carbohydrate component of this protein. The positive and negative controls are horseradish peroxidase and BSA, respectively. Escapin showed negative results.

Cloning and Expression of Escapin in Bacterial and Insect Cell: The escapin gene was cloned and expressed in both *E. coli* and insect cell systems.

*E. coli* System:
  Escapin was expressed in *E. coli*. Since most of the expressed protein formed an inclusion body, it was solubilized and purified in 8 M urea using a MonoQ 10/10 column.
  An antibody was made to this purified denatured Escapin. This antibody recognized recombinant Escapin and recombinant Escapin precursor in Western blots.
  Denatured Escapin purified from inclusion bodies was renatured by 100-fold dilution in buffer containing FAD, and then concentrated using a spin column.

Insect Cell System:
  This expressed protein was tested for antibacterial assay. The results showed that insect-cell-expressed Escapin inhibits 3-day old *E. coli*.

Throughout this application, various publications are referenced. The disclosures of these publications in their entireties are hereby incorporated by reference into this application in order to more fully describe the state of the art to which this invention pertains.

REFERENCES

1. Balaban, N. Q., J. Merrin, R. Chait, L. Kowalik, and S. Leibler. 2004. Bacterial persistence as a phenotypic switch. Science 305:1622-1625.
2. Butzke, D., N. Machuy, B. Thiede, R. Hurwitz, S. Goedert, and T. Rudel. 2004. Hydrogen peroxide produced by *Aplysia* ink toxin kills tumor cells independent of apoptosis via peroxiredoxin I sensitive pathways. Cell Death Differ. 11:608-617.
3. Chapman, D. J., and D. L. Fox. 1969. Bile pigment metabolism in the sea-hare *Aplysia*. J. Exp. Mar. Biol. Ecol. 4:71-78.
4. Cummins, S. F., A. E. Nichols, A. Amare, A. B. Hummon, J. V. Sweedler, and G. T. Nagle. 2004. Characterization of *Aplysia* enticin and temptin, two novel water-borne protein pheromones that act in concert with attractin to stimulate mate attraction. J. Biol. Chem. 279:25614-25622.
5. Du, X. Y., and K. J. Clemetson. 2002. Snake venom L-amino acid oxidases. Toxicon 40:659-665.
6. Ehara, T., S. Kitajima, N. Kanzawa, T. Tamiya, and T. Tsuchiya. 2002. Antimicrobial action of achacin is mediated by L-amino acid oxidase activity. FEBS Lett. 531:509-512.
7. Iguchi, S. M., T. Aikawa, and J. J. Matsumoto. 1982. Antibacterial activity of snail mucus mucin. Comp. Biochem. Physiol. 72A:571-574.
8. Iijima, R., J. Kisugi, and M. Yamazaki. 1995. Antifungal activity of aplysianin E, a cytotoxic protein of sea hare (*Aplysia kurodai*) eggs. Dev. Comp. Immunol. 19:13-19.
9. Iijima, R., J. Kisugi, and M. Yamazaki. 2003. L-Amino acid oxidase activity of an antineoplastic factor of a marine mollusk and its relationship to cytotoxicity. Dev. Comp. Immunol. 27:505-512.
10. Jimbo, M., F. Nakanishi, R. Sakai, K. Muramoto, and H. Kamiya. 2003. Characterization of L-amino acid oxidase and antimicrobial activity of aplysianin A, a sea hare-derived antitumor-antimicrobial protein. Fisheries Sci. 69:1240-1246.
11. Johnson, P. M. 2002. Multi-component chemical defense in seahares (Gastropoda: Opisthobranchia): antipredator compounds act as both honest and deceptive signals to multiple predator species. Dissertation, University of Washington.
12. Johnson, P. M., and A. O. D. Willows. 1999. Chemical defense in seahares (Gastropoda, Opisthobranchia, Anaspidea): multiple layers of protection from egg to adult. Mar. Freshwat. Behav. Physiol. 32:147-180.
13. Kamiya, H., K. Muramoto, R. Goto, M. Sakai, Y. Endo, and M. Yamazaki. 1989. Purification and characterization of an antibacterial and antineoplastic protein secretion of a sea hare, *Aplysia juliana*. Toxicon 27:1269-1277.
14. Kamiya, H., K. Muramoto, and M. Yamazaki. 1986. Aplysianin-A, an antibacterial and antineoplastic glycoprotein in the albumen gland of a sea hare, *Aplysia kurodai*. Experientia 42:1065-1067.
15. Kanzawa, N., S. Shintani, K. Ohta, S. Kitajima, T. Ehara, H. Kobayashi, H. Kizaki, and T. Tsuchiya. 2004. Achacin induces cell death in HeLa cells through two different mechanisms. Arch. Biochem. Biophys. 422:103-109.
16. Keren, I., N. Kaldalu, A. Spoering, Y. Wang, and K. Lewis. 2004. Persister cells and tolerance to antimicrobials. FEMS Microbiol. Lett. 230:13-18.
17. Kisugi, J., H. Ohye, H. Kamiya, and M. Yamazaki. 1989. Biopolymers from marine invertebrates. X. Mode of action of an antibacterial glycoprotein, aplysianin E, from eggs of a sea hare, *Aplysia kurodai*. Chem. Pharm. Bull. (Tokyo) 37:3050-3053.
18. Kubota, Y., Y. Watanabe, H. Otsuka, T. Tamiya, T. Tsuchiya, and J. J. Matsumoto. 1985. Purification and characterization of an antibacterial factor from snail mucus. Comp. Biochem. Physiol. 82C:345-348.
19. Light, D. R., C. Walsh, and M. A. Marletta. 1980. Analytical and preparative high-performance liquid chromatography separation of flavin and flavin analog coenzymes. Anal. Biochem. 109:87-93.
20. Lu, Q. M., Q. Wei, Y. Jin, J. F. Wei, W. Y. Wang, and Y. L. Xiong. 2002. L-amino acid oxidase from *Trimeresurus jerdonii* snake venom: purification, characterization, platelet aggregation-inducing and antibacterial effects. J Nat Toxins 11:345-352.
21. MacColl, R., J. Galivan, D. S. Berns, Z. Nimec, D. Guard-Friar, and D. Wagoner. 1990. The chromophore and polypeptide composition of *Aplysia* ink. Biol. Bull. 179:326-331.
22. MacHeroux, P., O. Seth, C. Bollschweiler, M. Schwarz, M. Kurfurst, L. C. Au, and S. Ghisla. 2001. L-Amino-acid oxidase from the Malayan pit viper *Calloselasma rhodostoma*. Comparative sequence analysis and characterization of active and inactive forms of the enzyme. Eur. J. Biochem. 268:1679-1686.
23. Melo, V. M., A. B. Duarte, A. F. Carvalho, E. A. Siebra, and I. M. Vasconcelos. 2000. Purification of a novel antibacterial and haemagglutinating protein from the purple gland of the sea hare, *Aplysia dactylomela* Rang, 1828. Toxicon 38:1415-1427.
24. Melo, V. M., A. M. Fonseca, I. M. Vasconcelos, and A. F. Carvalho. 1998. Toxic, antimicrobial and hemagglutinating activities of the purple fluid of the sea hare *Aplysia dactylomela* Rang, 1828. Braz. J. Med. Biol. Res. 31:785-791.
25. Nolen, T. G., P. M. Johnson, C. E. Kicklighter, and T. Capo. 1995. Ink secretion by the marine snail *Aplysia californica* enhances its ability to escape from a natural predator. J. Comp. Physiol. A 176:239-254.
26. Obara, K, H. Otsuka-Fuchino, N. Sattayasai, Y. Nonomura, T. Tsuchiya, and T. Tamiya. 1992. Molecular cloning of the antibacterial protein of the giant African snail, *Achatina fulica* Ferussac. Eur. J. Biochem. 209:1-6.
27. Ogawa, M., S. Nakamura, T. Atsuchi, T. Tamiya, T. Tsuchiya, and S. Nakai. 1999. Macromolecular antimicrobial glycoprotein, achacin, expressed in a methylotrophic yeast *Pichia pastoris*. FEBS Lett. 448:41-44.
28. Otsuka-Fuchino, H., Y. Watanabe, C. Hirakawa, J. Takeda, T. Tamiya, J. J. Matsumoto, and T. Tsuchiya. 1993. Morphological aspects of achacin-treated bacteria. Comp. Biochem. Physiol. 104C:37-42.
29. Otsuka-Fuchino, H., Y. Watanabe, C. Hirakawa, T. Tamiya, J. J. Matsumoto, and T. Tsuchiya. 1992. Bactericidal action of a glycoprotein from the body surface mucus of giant African snail. Comp. Biochem. Physiol. 101C:607-613.
30. Petzelt, C., G. Joswig, H. Stammer, and D. Werner. 2002. Cytotoxic cyplasin of the sea hare, *Aplysia punctata*, cDNA cloning, and expression of bioactive recombinants in insect cells. Neoplasia 4:49-59.
31. Suhr, S. M., and D. S. Kim. 1996. Identification of the snake venom substance that induces apoptosis. Biochem. Biophys. Res. Commun. 224:134-139.
32. Takamatsu, N., T. Shiba, K. Muramoto, and H. Kamiya. 1995. Molecular cloning of the defense factor in the albumen gland of the sea hare *Aplysia kurodai*. FEBS Lett. 377:373-376.
33. Torii, S., M. Naito, and T. Tsuruo. 1997. Apoxin I, a novel apoptosis-inducing factor with L-amino acid oxidase activity purified from Western diamondback rattlesnake venom. J. Biol. Chem. 272:9539-9542.
34. Torii, S., K. Yamane, T. Mashima, N. Haga, K. Yamamoto, J. W. Fox, M. Naito, and T. Tsuruo. 2000. Molecular cloning and functional analysis of apoxin I, a snake venom-derived apoptosis-inducing factor with L-amino acid oxidase activity. Biochemistry 39:3197-3205.
35. Troxler, R. R., G. D. Offner, and T. R. Capo. 1981. Structural studies on aplysioviolin. Biol. Bull. 161:339 (abstract).
36. Wei, J. F., Q. Wei, Q. M. Lu, H. Tai, Y. Jin, W. Y. Wang, and Y. L. Xiong. 2003. Purification, characterization and biological activity of an L-amino acid oxidase from *Trimeresurus mucrosquamatus* venom. Sheng Wu Hua Xue Yu Sheng Wu Wu Li Xue Bao (Shanghai) 35:219-224.
37. Whitby, L. G. 1953. A new method for preparing flavin-adenine dinucleotide. Biochem. J. 54:437-442.
38. Yamazaki, M. 1993. Antitumor and antimicrobial glycoproteins from sea hares. Comp. Biochem. Physiol. 105C:141-146.
39. Yamazaki, M., K. Kimura, J. Kisugi, K. Muramoto, and H. Kamiya. 1989. Isolation and characterization of a novel cytolytic factor in purple fluid of the sea hare, *Aplysia kurodai*. Cancer Res. 49:3834-3838.
40. Yamazaki, M., H. Ohye, J. Kisugi, and H. Kamiya. 1990. Bacteriostatic and cytolytic activity of purple fluid from the sea hare. Dev. Comp. Immunol. 14:379-383.
41. Yamazaki, M., S. Tansho, J. Kisugi, K. Muramoto, and H. Kamiya. 1989. Purification and characterization of a cytolytic protein from purple fluid of the sea hare, *Dolabella auricularia*. Chem. Pharm. Bull. (Tokyo) 37:2179-2182.

TABLE 2

Antimicrobial activity of wild-type escapin. The minimum inhibition concentration (MIC) of escapin against various microbes, determined by measuring inhibition of growth on plates of solid media.

| Microbial species | MIC (µg/ml) |
|---|---|
| Gram-negative Bacteria | |
| *Escherichia coli* (MC4100) | 0.62 |
| *Salmonella typhimurium* AA 140 | 0.62 |
| *Pseudomonas aeruginosa* PAO1 | 0.31 |
| *Vibrio harveyi* BB170 | 0.25 |
| Gram-positive Bacteria | |
| *Staphylococcus aureus* 6835 | 0.31 |
| *Streptococcus pyogenes* NZ131 | 0.62 |
| *Bacillus subtilis* 168 | 2.50 |
| *Bacillus subtilis* WB600 | 2.50 |
| Yeast | |
| *Candida krusei* | 5.0 |
| *Saccharomyces cerevisiae* BY4761 | 5.0 |
| Fungus | |
| *Cladosporium notitalics* | 62 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated polypeptide comprising the amino acid sequence identified as SEQ ID NO:1.

2. An isolated polypeptide comprising a fragment of the polypeptide identified as SEQ ID NO:1, wherein the fragment has the amino acid sequence identified as SEQ ID NO:19, and wherein the polypeptide inhibits growth of a microbe on a surface.

3. An isolated polypeptide comprising the amino acid sequence at least 95% identical to a sequence identified as SEQ ID NO:1, and wherein the polypeptide inhibits growth of a microbe on a surface.

4. An isolated polypeptide consisting of the amino acid sequence identified as SEQ ID NO:1.

5. The polypeptide of claim 4, wherein the polypeptide is isolated from *Aplysia californica*.

* * * * *

SEQUENCE LISTING

<160> NUMBER OF SEQ ID NOS: 23

<210> SEQ ID NO 1
<211> LENGTH: 529
<212> TYPE: PRT
<213> ORGANISM: Artificial Sequence -continued

```
<220> FEATURE:
<223> OTHER INFORMATION: Description of artificial sequence; note =
      synthetic construct

<400> SEQUENCE: 1

Met Ser Ser Ala Phe Leu Leu Leu Ala Cys Ala Leu Val Ile Ser Val
 1               5                  10                  15

His Ala Asp Gly Val Cys Arg Asn Arg Arg Gln Cys Asn Lys Glu Val
            20                  25                  30

Cys Gly Ser Ser Tyr Asp Val Ala Ile Val Gly Ala Gly Pro Gly Gly
        35                  40                  45

Ala Asn Ser Ala Tyr Met Leu Arg Glu Ser Gly Leu Asp Ile Ala Val
 50                  55                  60

Phe Glu Tyr Ser Asp Arg Val Gly Gly Arg Leu Phe Thr Tyr Gln Leu
 65                  70                  75                  80

Pro Asn Thr Pro Asp Val Asn Leu Glu Ile Gly Gly Met Arg Phe Ile
                85                  90                  95

Glu Gly Ala Met His Arg Leu Trp Lys Val Ile Ser Glu Leu Gly Leu
            100                 105                 110

Thr Pro Lys Val Phe Lys Glu Gly Phe Lys Glu Gly Arg Gln Arg
        115                 120                 125

Phe Tyr Leu Arg Gly Gln Ser Leu Thr Lys Lys Gln Val Lys Ser Gly
130                 135                 140

Asp Val Pro Tyr Asp Leu Ser Pro Glu Glu Lys Ala Asn Gln Gly Arg
145                 150                 155                 160

Leu Val Glu Tyr Tyr Leu Glu Lys Leu Thr Gly Leu Gln Leu Asn Gly
                165                 170                 175

Gly Pro Leu Lys Arg Glu Val Lys Leu Thr Val Pro Asp Gly Arg Phe
            180                 185                 190

Leu Tyr Asp Leu Thr Phe Asp Glu Ala Leu Asp Leu Val Asp Glu Gly
        195                 200                 205

Lys Glu Phe Ala Arg Asp Thr His Val Phe Thr Ser Glu Val Thr Leu
210                 215                 220

Asp Ala Ser Ala Ile Ser Ile Phe Asp Asp His Leu Gly Glu Asp Tyr
225                 230                 235                 240

Tyr Gly Ser Glu Ile Tyr Thr Leu Glu Glu Gly Met Ser Ser Val Pro
                245                 250                 255

Gln Gly Leu Leu Gln Thr Phe Leu Asp Ala Ala Lys Ser Asn Glu Phe
            260                 265                 270

Phe Pro Asn Asn His Leu Lys Ala Leu Arg Arg Arg Thr Asn Gly Gln
        275                 280                 285

Tyr Val Leu Tyr Phe Glu Pro Thr Thr Ser Lys Asp Gly Gln Thr Thr
290                 295                 300

Ile Asn Tyr Leu Glu Pro Leu Lys Val Val Cys Ala Gln Arg Val Ile
305                 310                 315                 320

Leu Ala Met Pro Val Tyr Ala Leu Arg Gln Leu Asp Trp Ser Gln Leu
                325                 330                 335

Arg Asn Asp Arg Ala Thr Gln Ala Tyr Arg Ala Val Arg Pro Met Pro
            340                 345                 350

Ala Ser Lys Val Phe Met Thr Phe Asp Gln Pro Trp Trp Leu Gln Asn
        355                 360                 365

Glu Arg Lys Ser Trp Val Thr Lys Ser Asp Ala Leu Phe Ser Gln Met
370                 375                 380
```

-continued

Tyr Asp Trp Gln Lys Ser Glu Ala Ser Gly Asp Tyr Ile Leu Ile Ala
385                 390                 395                 400

Ser Tyr Ala Asp Gly Leu Lys Ala Gln Tyr Leu Arg Glu Leu Lys Asn
            405                 410                 415

Gln Gly Glu Asp Ile Pro Gly Ser Asp Pro Gly Tyr Asn Gln Val Thr
        420                 425                 430

Val Pro Leu Lys Asp Ala Ile His Leu Thr Glu Ala Tyr Gly Val Glu
            435                 440                 445

Arg Asp Ser Ile Pro Glu Pro Val Thr Ala Ala Ser Gln Phe Trp Thr
        450                 455                 460

Asp Tyr Pro Phe Gly Cys Gly Trp Ile Thr Trp Arg Ala Gly Tyr His
465                 470                 475                 480

Phe Asp Asp Val Ile Ser Thr Met Arg Arg Pro Ser Leu Lys Asp Glu
                485                 490                 495

Val Tyr Val Val Gly Ser Asp Tyr Ser Trp Gly Leu Ile Ser Ser Trp
            500                 505                 510

Ile Glu Gly Ala Leu Glu Thr Ser Glu Asn Val Ile Asn Asp Tyr Phe
        515                 520                 525

Leu

<210> SEQ ID NO 2
<211> LENGTH: 1605
<212> TYPE: DNA
<213> ORGANISM: Artificial Sequence
<220> FEATURE:
<223> OTHER INFORMATION: Description of artificial sequence; note = synthetic construct

<400> SEQUENCE: 2

| | |
|---|---|
| atgtcgtctg ctttccttct cctggcttgt gcgctggtca tctctgtcca cgccgacggc | 60 |
| gtctgcagaa acaggcgtca gtgtaacaaa gaggtgtgcg gttcctctta tgacgtggcc | 120 |
| atcgtggggg cggggccagg gggagctaac tccgcctaca tgctgaggga gtctggcctg | 180 |
| gacatcgctg tgttcgagta ctctgaccgg gtgggtggcc gtctgttcac ctaccagctg | 240 |
| cccaacacac ccgacgtgaa cctggagatt ggcggcatga ggttcatcga gggcgccatg | 300 |
| cacagactct ggaaagtcat ttcagaactc ggactgaccc ccaaggtgtt caaggaaggt | 360 |
| ttcggcaagg agggcagaca gaggttctac ctacgtggac agagcctgac caagaaacag | 420 |
| gtcaagagcg ggacgtacc ctatgacctc agcccggagg agaaggccaa ccagggacgt | 480 |
| ctggtcgaat actacctgga gaaactgacc ggattacagc tcaacggcgg accactcaaa | 540 |
| cgggaggtgg cgctcaaact gaccgtgccg gacggcagat cctctatga cctcacgttt | 600 |
| gacgaagccc tggacctggt ggcctcccct gagggcaaag agttcgcccg agacacgcac | 660 |
| gtgtttacct cagaggtcac actggacgcg tcggctatct ccatcttcga tgaccacctg | 720 |
| ggagaggact actatggcag tgagatctac accctggagg aaggaatgtc ttctgtacca | 780 |
| caaggactgc tacagacttt tctggacgcc gctaaatcca acgagttctt ccccaacaac | 840 |
| cacctgaagg ctctgagacg gaggaccaat ggtcagtatg tcctgtactt tgagcccacc | 900 |
| acgtccaagg atggacaaac caccatcaac tacctggaac ccctgaaggt tgtgtgtgct | 960 |
| cagagagtca tcctggccat gccggtctac gctctcagac aactgactg gtcacaactc | 1020 |
| agaaatgacc gcgccaccca agcgtacaga gccgtgcgtc ctatgcctgc agtaaagtc | 1080 |
| tttatgacct tgaccagcc ctggtggttg cagaatgaga ggaaatcttg gtaaccaaa | 1140 |
| tcagacgcgc ttttcagcca aatgtatgac tggcagaagt ctgaggcgtc tggagattac | 1200 |

```
atcctgatcg ccagctacgc cgacggcctc aaagcccagt acttgcggga gctgaagaac    1260
cagggagagg acatcccagg ctctgacccc ggctacaacc aggtcaccgt acccctcaag    1320
gacgccattc ttgaacacct caccgaggct tacggcgtgg agcgagactc gatcccagaa    1380
cccgtgactg ctgcctccca gttttggaca gactacccgt ttggctgcgg ctggatcacc    1440
tggagggccg gttaccattt tgatgacgtc atcagcacca tgcgtcgccc gtcactgaaa    1500
gatgaagtct acgtggtagg atcggattac tcctggggac ttatctcctc ctggatagag    1560
ggcgctcttg agacatcgga aaacgtcatc aacgactact cctc                     1605
```

<210> SEQ ID NO 3
<211> LENGTH: 25
<212> TYPE: DNA
<213> ORGANISM: Artificial Sequence
<220> FEATURE:
<223> OTHER INFORMATION: Description of artificial sequence; note = synthetic construct

<400> SEQUENCE: 3
gttcacgtcg ggtgtgttgg gcagc                                          25

<210> SEQ ID NO 4
<211> LENGTH: 20
<212> TYPE: DNA
<213> ORGANISM: Artificial Sequence
<220> FEATURE:
<223> OTHER INFORMATION: Description of artificial sequence; note = synthetic construct

<400> SEQUENCE: 4
tggtaggtga acagacggcc                                                20

<210> SEQ ID NO 5
<211> LENGTH: 19
<212> TYPE: DNA
<213> ORGANISM: Artificial Sequence
<220> FEATURE:
<223> OTHER INFORMATION: Description of artificial sequence; note = synthetic construct

<400> SEQUENCE: 5
ccggtcgcag aactcgaaa                                                 19

<210> SEQ ID NO 6
<211> LENGTH: 20
<212> TYPE: DNA
<213> ORGANISM: Artificial Sequence
<220> FEATURE:
<223> OTHER INFORMATION: Description of artificial sequence; note = synthetic construct

<400> SEQUENCE: 6
atctacaccc tggaggaagg                                                20

<210> SEQ ID NO 7
<211> LENGTH: 26
<212> TYPE: DNA
<213> ORGANISM: Artificial Sequence
<220> FEATURE:
<223> OTHER INFORMATION: Description of artificial sequence; note = synthetic construct

<400> SEQUENCE: 7
ggatcccatg tcgtctgctt tccttc                                         26

```
<210> SEQ ID NO 8
<211> LENGTH: 26
<212> TYPE: DNA
<213> ORGANISM: Artificial Sequence
<220> FEATURE:
<223> OTHER INFORMATION: Description of artificial sequence; note =
      synthetic construct

<400> SEQUENCE: 8
aagcttgagg aagtagtcgt tgatga                                          26

<210> SEQ ID NO 9
<211> LENGTH: 14
<212> TYPE: PRT
<213> ORGANISM: Artificial Sequence
<220> FEATURE:
<223> OTHER INFORMATION: Description of artificial sequence; note =
      synthetic construct

<400> SEQUENCE: 9

Glu Ser Gly Leu Asp Ile Ala Val Phe Glu Tyr Ser Asp Arg
 1               5                  10

<210> SEQ ID NO 10
<211> LENGTH: 15
<212> TYPE: PRT
<213> ORGANISM: Artificial Sequence
<220> FEATURE:
<223> OTHER INFORMATION: Description of artificial sequence; note =
      synthetic construct

<400> SEQUENCE: 10

Val Phe Met Thr Phe Asp Gln Pro Trp Trp Leu Gln Asn Glu Arg
 1               5                  10                  15

<210> SEQ ID NO 11
<211> LENGTH: 20
<212> TYPE: DNA
<213> ORGANISM: Artificial Sequence
<220> FEATURE:
<223> OTHER INFORMATION: Description of artificial sequence; note =
      synthetic construct

<400> SEQUENCE: 11
ttcgagttct gcgaccgggt                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of artificial sequence; note =
      synthetic construct

<400> SEQUENCE: 12
tcatgsaagt ggactggccc                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of artificial sequence; note =
      synthetic construct

<400> SEQUENCE: 13
tgacctttga ccagccttgg                                                 20
```

```
<210> SEQ ID NO 14
<211> LENGTH: 20
<212> TYPE: DNA
<213> ORGANISM: Artificial Sequence
<220> FEATURE:
<223> OTHER INFORMATION: Description of artificial sequence; note =
      synthetic construct

<400> SEQUENCE: 14
agacggtggt tgcacgttgt                                              20

<210> SEQ ID NO 15
<211> LENGTH: 20
<212> TYPE: DNA
<213> ORGANISM: Artificial Sequence
<220> FEATURE:
<223> OTHER INFORMATION: Description of artificial sequence; note =
      synthetic construct

<400> SEQUENCE: 15
ccaaggctgg tcaaaggtca                                              20

<210> SEQ ID NO 16
<211> LENGTH: 20
<212> TYPE: DNA
<213> ORGANISM: Artificial Sequence
<220> FEATURE:
<223> OTHER INFORMATION: Description of artificial sequence; note =
      synthetic construct

<400> SEQUENCE: 16
agtccccaga aacgttggac                                              20

<210> SEQ ID NO 17
<211> LENGTH: 17
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: 3,10
<223> OTHER INFORMATION: n can be either a, c,g, or t(u)

<400> SEQUENCE: 17
cgnaactcgn gactcag                                                 17

<210> SEQ ID NO 18
<211> LENGTH: 24
<212> TYPE: DNA
<213> ORGANISM: Artificial Sequence
<220> FEATURE:
<223> OTHER INFORMATION: Description of artificial sequence; note =
      synthetic construct
<220> FEATURE:
<221> NAME/KEY: misc_feature
<222> LOCATION: 7,10,13
<223> OTHER INFORMATION: n can be either a,c,g,t(u)

<400> SEQUENCE: 18
gagatcnggn ctngactata ctgc                                         24

<210> SEQ ID NO 19
<211> LENGTH: 512
<212> TYPE: PRT
<213> ORGANISM: Artificial Sequence
```

```
<220> FEATURE:
<223> OTHER INFORMATION: Description of artificial sequence; note =
      synthetic construct

<400> SEQUENCE: 19

Met Asp Gly Val Cys Arg Asn Arg Arg Gln Cys Asn Lys Glu Val Cys
 1               5                  10                  15

Gly Ser Ser Tyr Asp Val Ala Ile Val Gly Ala Gly Pro Gly Gly Ala
            20                  25                  30

Asn Ser Ala Tyr Met Leu Arg Glu Ser Gly Leu Asp Ile Ala Val Phe
        35                  40                  45

Glu Tyr Ser Asp Arg Val Gly Gly Arg Leu Phe Thr Tyr Gln Leu Pro
    50                  55                  60

Asn Thr Pro Asp Val Asn Leu Glu Ile Gly Gly Met Arg Phe Ile Glu
65                  70                  75                  80

Gly Ala Met His Arg Leu Trp Lys Val Ile Ser Glu Leu Gly Leu Thr
                85                  90                  95

Pro Lys Val Phe Lys Glu Gly Phe Gly Lys Glu Gly Arg Gln Arg Phe
            100                 105                 110

Tyr Leu Arg Gly Gln Ser Leu Thr Lys Lys Gln Val Lys Ser Gly Asp
        115                 120                 125

Val Pro Tyr Asp Leu Ser Pro Glu Lys Ala Asn Gln Gly Arg Leu
130                 135                 140

Val Glu Tyr Tyr Leu Glu Lys Leu Thr Gly Leu Gln Leu Asn Gly Gly
145                 150                 155                 160

Pro Leu Lys Arg Glu Val Lys Leu Thr Val Pro Asp Gly Arg Phe Leu
                165                 170                 175

Tyr Asp Leu Thr Phe Asp Glu Ala Leu Asp Leu Val Asp Glu Gly Lys
            180                 185                 190

Glu Phe Ala Arg Asp Thr His Val Phe Thr Ser Glu Val Thr Leu Asp
        195                 200                 205

Ala Ser Ala Ile Ser Ile Phe Asp Asp His Leu Gly Glu Asp Tyr Tyr
    210                 215                 220

Gly Ser Glu Ile Tyr Thr Leu Glu Glu Gly Met Ser Ser Val Pro Gln
225                 230                 235                 240

Gly Leu Leu Gln Thr Phe Leu Asp Ala Ala Lys Ser Asn Glu Phe Phe
                245                 250                 255

Pro Asn Asn His Leu Lys Ala Leu Arg Arg Thr Asn Gly Gln Tyr
            260                 265                 270

Val Leu Tyr Phe Glu Pro Thr Thr Ser Lys Asp Gly Gln Thr Thr Ile
        275                 280                 285

Asn Tyr Leu Glu Pro Leu Lys Val Val Cys Ala Gln Arg Val Ile Leu
    290                 295                 300

Ala Met Pro Val Tyr Ala Leu Arg Gln Leu Asp Trp Ser Gln Leu Arg
305                 310                 315                 320

Asn Asp Arg Ala Thr Gln Ala Tyr Arg Ala Val Arg Pro Met Pro Ala
                325                 330                 335

Ser Lys Val Phe Met Thr Phe Asp Gln Pro Trp Trp Leu Gln Asn Glu
            340                 345                 350

Arg Lys Ser Trp Val Thr Lys Ser Asp Ala Leu Phe Ser Gln Met Tyr
        355                 360                 365

Asp Trp Gln Lys Ser Glu Ala Ser Gly Asp Tyr Ile Leu Ile Ala Ser
    370                 375                 380
```

```
Tyr Ala Asp Gly Leu Lys Ala Gln Tyr Leu Arg Glu Leu Lys Asn Gln
385                 390                 395                 400

Gly Glu Asp Ile Pro Gly Ser Asp Pro Gly Tyr Asn Gln Val Thr Val
            405                 410                 415

Pro Leu Lys Asp Ala Ile His Leu Thr Glu Ala Tyr Gly Val Glu Arg
            420                 425                 430

Asp Ser Ile Pro Glu Pro Val Thr Ala Ala Ser Gln Phe Trp Thr Asp
            435                 440                 445

Tyr Pro Phe Gly Cys Gly Trp Ile Thr Trp Arg Ala Gly Tyr His Phe
            450                 455                 460

Asp Asp Val Ile Ser Thr Met Arg Arg Pro Ser Leu Lys Asp Glu Val
465                 470                 475                 480

Tyr Val Val Gly Ser Asp Tyr Ser Trp Gly Leu Ile Ser Ser Trp Ile
                485                 490                 495

Glu Gly Ala Leu Glu Thr Ser Glu Asn Val Ile Asn Asp Tyr Phe Leu
                500                 505                 510
```

<210> SEQ ID NO 20
<211> LENGTH: 1554
<212> TYPE: DNA
<213> ORGANISM: Artificial Sequence
<220> FEATURE:
<223> OTHER INFORMATION: Description of artificial sequence; note = synthetic construct

<400> SEQUENCE: 20

```
atggacggcg tctgcagaaa caggcgtcag tgtaacaaag aggtgtgcgg ttcctcttat    60
gacgtggcca tcgtgggggc ggggccaggg ggagctaact ccgcctacat gctgagggag   120
tctggcctgg acatcgctgt gttcgagtac tctgaccggg tgggtggccg tctgttcacc   180
taccagctgc ccaacacacc cgacgtgaac ctggagattg cggcatgag gttcatcgag   240 ggcgccatgc acagactctg gaaagtcatt tcagaactcg gactgacccc caaggtgttc   300
aaggaaggtt tcggcaagga gggcagacag aggttctacc tacgtggaca gagcctgacc   360
aagaaacagg tcaagagcgg ggacgtaccc tatgacctca gcccggagga aaggccaaac   420
cagggacgtc tggtcgaata ctacctggag aaactgaccg gattacagct caacggcgga   480
ccactcaaac gggaggtggc gctcaaactg accgtgccgg acggcagatt cctctatgac   540
ctcacgtttg acgaagccct ggacctggtg gcctccctg agggcaaaga gttcgcccga   600
gacacgcacg tgtttacctc agaggtcaca ctggacgcgt cggctatctc catcttcgat   660
gaccacctgg agaggactac tatggcagt gagatctaca ccctggagga aggaatgtct   720
tctgtaccac aaggactgct acagactttt ctggacgccg ctaaatccaa cgagttcttc   780
cccaacaacc acctgaaggc tctgagacgg aggaccaatg gtcagtatgt cctgtacttt   840
gagcccacca cgtccaagga tggacaaacc accatcaact acctggaacc cctgaaggtt   900
gtgtgtgctc agagagtcat cctggccatg ccggtctacg ctctcagaca actggactgg   960
tcacaactca gaaatgaccg cgccaccaa gcgtacagag ccgtgcgtcc tatgcctgcc  1020
agtaaagtct ttatgacctt tgaccagccc tggtggttgc agaatgagag gaaatcttgg  1080
gtaaccaaat cagacgcgct tttcagccaa atgtatgact ggcagaagtc tgaggcgtct  1140
ggagattaca tcctgatcgc cagctacgcc gacggcctca agcccagta cttgcgggag  1200 ctgaagaacc agggagagga catcccaggc tctgaccccg gctacaacca ggtcaccgta  1260 ccctcaagg acgccattct tgaacacctc accgaggctt acggcgtgga gcgagactcg  1320
```

```
atcccagaac cgtgactgc tgcctcccag ttttggacag actacccgtt tggctgcggc    1380
tggatcacct ggagggccgg ttaccatttt gatgacgtca tcagcaccat gcgtcgcccg    1440
tcactgaaag atgaagtcta cgtggtagga tcggattact cctggggact tatctcctcc    1500
tggatagagg gcgctcttga gacatcggaa aacgtcatca cgactactt cctc           1554
```

<210> SEQ ID NO 21
<211> LENGTH: 305
<212> TYPE: PRT
<213> ORGANISM: Artificial Sequence
<220> FEATURE:
<223> OTHER INFORMATION: Description of artificial sequence; note = synthetic construct

<400> SEQUENCE: 21

```
Met Asp Gly Val Cys Arg Asn Arg Arg Gln Cys Asn Lys Glu Val Cys
 1               5                  10                  15

Gly Ser Ser Tyr Asp Val Ala Ile Val Gly Ala Gly Pro Gly Gly Ala
                20                  25                  30

Asn Ser Ala Tyr Met Leu Arg Glu Ser Gly Leu Asp Ile Ala Val Phe
            35                  40                  45

Glu Tyr Ser Asp Arg Val Gly Gly Arg Leu Phe Thr Tyr Gln Leu Pro
    50                  55                  60

Asn Thr Pro Asp Val Asn Leu Glu Ile Gly Gly Met Arg Phe Ile Glu
65                  70                  75                  80

Gly Ala Met His Arg Leu Trp Lys Val Ile Ser Glu Leu Gly Leu Thr
                85                  90                  95

Pro Lys Val Phe Lys Glu Gly Phe Gly Lys Glu Gly Arg Gln Arg Phe
            100                 105                 110

Tyr Leu Arg Gly Gln Ser Leu Thr Lys Lys Gln Val Lys Ser Gly Asp
        115                 120                 125

Val Pro Tyr Asp Leu Ser Pro Glu Glu Lys Ala Asn Gln Gly Arg Leu
    130                 135                 140

Val Glu Tyr Tyr Leu Glu Lys Leu Thr Gly Leu Gln Leu Asn Gly Gly
145                 150                 155                 160

Pro Leu Lys Arg Glu Val Lys Leu Thr Val Pro Asp Gly Arg Phe Leu
                165                 170                 175

Tyr Asp Leu Thr Phe Asp Glu Ala Leu Asp Leu Val Asp Glu Gly Lys
            180                 185                 190

Glu Phe Ala Arg Asp Thr His Val Phe Thr Ser Glu Val Thr Leu Asp
        195                 200                 205

Ala Ser Ala Ile Ser Ile Phe Asp Asp His Leu Gly Glu Asp Tyr Tyr
    210                 215                 220

Gly Ser Glu Ile Tyr Thr Leu Glu Glu Gly Met Ser Ser Val Pro Gln
225                 230                 235                 240

Gly Leu Leu Gln Thr Phe Leu Asp Ala Ala Lys Ser Asn Glu Phe Phe
                245                 250                 255

Pro Asn Asn His Leu Lys Ala Leu Arg Arg Arg Thr Asn Gly Gln Tyr
            260                 265                 270

Val Leu Tyr Phe Glu Pro Thr Thr Ser Lys Asp Gly Gln Thr Thr Ile
        275                 280                 285

Asn Tyr Leu Glu Pro Leu Lys Val Val Cys Ala Gln Arg Val Ile Leu
    290                 295                 300

Ala
305
```

-continued

<210> SEQ ID NO 22
<211> LENGTH: 627
<212> TYPE: DNA
<213> ORGANISM: Artificial Sequence
<220> FEATURE:
<223> OTHER INFORMATION: Description of artificial sequence; note = synthetic construct

<400> SEQUENCE: 22

```
atgccggtct acgctctcag acaactggac tggtcacaac tcagaaatga ccgcgccacc      60
caagcgtaca gagccgtgcg tcctatgcct gccagtaaag tctttatgac ctttgaccag     120
ccctggtggt tgcagaatga gaggaaatct tgggtaacca atcagacgc gcttttcagc      180 caaatgtatg actggcagaa gtctgaggcg tctggagatt acatcctgat cgccagctac     240
gccgacggcc tcaaagccca gtacttgcgg gagctgaaga accagggaga ggacatccca    300
ggctctgacc ccggctacaa ccaggtcacc gtacccctca aggacgccat tcttgaacac    360
ctcaccgagg cttacggcgt ggagcgagac tcgatcccag aacccgtgac tgctgcctcc    420
cagttttgga cagactaccc gtttggctgc ggctggatca cctggagggc cggttaccat    480
tttgatgacg tcatcagcac catgcgtcgc ccgtcactga agatgaagt ctacgtggta    540 ggatcggatt actcctgggg acttatctcc tcctggatag agggcgctct tgagacatcg    600
gaaaacgtca tcaacgacta cttcctc                                        627
```

<210> SEQ ID NO 23
<211> LENGTH: 529
<212> TYPE: PRT
<213> ORGANISM: Artificial Sequence
<220> FEATURE:
<223> OTHER INFORMATION: Description of artificial sequence; note = synthetic construct

<400> SEQUENCE: 23

```
Met Ser Ser Ala Phe Leu Leu Ala Cys Ala Leu Val Ile Ser Val
  1               5                  10                  15

His Ala Asp Gly Val Cys Arg Asn Arg Arg Gln Cys Asn Lys Glu Val
             20                  25                  30

Cys Gly Ser Ser Tyr Asp Val Ala Ile Val Gly Ala Gly Pro Gly Gly
         35                  40                  45

Ala Asn Ser Ala Tyr Met Leu Arg Glu Ser Gly Leu Asp Ile Ala Val
     50                  55                  60

Phe Glu Tyr Ser Asp Arg Val Gly Gly Arg Leu Phe Thr Tyr Gln Leu
 65                  70                  75                  80

Pro Asn Thr Pro Asp Val Asn Leu Glu Ile Gly Gly Met Arg Phe Ile
                 85                  90                  95

Glu Gly Ala Met His Arg Leu Trp Lys Val Ile Ser Glu Leu Gly Leu
            100                 105                 110

Thr Pro Lys Val Phe Lys Glu Gly Phe Gly Lys Glu Gly Arg Gln Arg
        115                 120                 125

Phe Tyr Leu Arg Gly Gln Ser Leu Thr Lys Lys Gln Val Lys Ser Gly
    130                 135                 140

Asp Val Pro Tyr Asp Leu Ser Pro Glu Glu Lys Ala Asn Gln Gly Arg
145                 150                 155                 160

Leu Val Glu Tyr Tyr Leu Glu Lys Leu Thr Gly Leu Gln Leu Asn Gly
                165                 170                 175

Gly Pro Leu Lys Arg Glu Val Lys Leu Thr Val Pro Asp Gly Arg Phe
            180                 185                 190
```

```
Leu Tyr Asp Leu Thr Phe Asp Glu Ala Leu Asp Leu Val Asp Glu Gly
            195                 200                 205

Lys Glu Phe Ala Arg Asp Thr His Val Phe Thr Ser Glu Val Thr Leu
        210                 215                 220

Asp Ala Ser Ala Ile Ser Ile Phe Asp Asp His Leu Gly Glu Asp Tyr
225                 230                 235                 240

Tyr Gly Ser Glu Ile Tyr Thr Leu Glu Glu Gly Met Ser Ser Val Pro
                245                 250                 255

Gln Gly Leu Leu Gln Thr Phe Leu Asp Ala Ala Lys Ser Asn Glu Phe
            260                 265                 270

Phe Pro Asn Asn His Leu Lys Ala Leu Arg Arg Arg Thr Asn Gly Gln
            275                 280                 285

Tyr Val Leu Tyr Phe Glu Pro Thr Thr Ser Lys Asp Gly Gln Thr Thr
        290                 295                 300

Ile Asn Tyr Leu Glu Pro Leu Lys Val Val Cys Ala Gln Arg Val Ile
305                 310                 315                 320

Leu Ala Met Pro Val Tyr Ala Leu Arg Gln Leu Asp Trp Ser Gln Leu
                325                 330                 335

Arg Asn Asp Arg Ala Thr Gln Ala Tyr Arg Ala Val Arg Pro Met Pro
            340                 345                 350

Ala Ser Lys Val Phe Met Thr Phe Asp Gln Pro Trp Trp Leu Gln Asn
            355                 360                 365

Glu Arg Lys Ser Trp Val Thr Lys Ser Asp Ala Leu Phe Ser Gln Met
        370                 375                 380

Tyr Asp Trp Gln Lys Ser Glu Ala Ser Gly Asp Tyr Ile Leu Ile Ala
385                 390                 395                 400

Ser Tyr Ala Asp Gly Leu Lys Ala Gln Tyr Leu Arg Glu Leu Lys Asn
                405                 410                 415

Gln Gly Glu Asp Ile Pro Gly Ser Asp Pro Gly Tyr Asn Gln Val Thr
            420                 425                 430

Val Pro Leu Lys Asp Ala Ile His Leu Thr Glu Ala Tyr Gly Val Glu
            435                 440                 445

Arg Asp Ser Ile Pro Glu Pro Val Thr Ala Ala Ser Gln Phe Trp Thr
        450                 455                 460

Asp Tyr Pro Phe Gly Cys Gly Trp Ile Thr Trp Arg Ala Gly Tyr His
465                 470                 475                 480

Phe Asp Asp Val Ile Ser Thr Met Arg Arg Pro Ser Leu Lys Asp Glu
                485                 490                 495

Val Tyr Val Val Gly Ser Asp Tyr Ser Trp Gly Leu Ile Ser Ser Trp
            500                 505                 510

Ile Glu Gly Ala Leu Glu Thr Ser Glu Asn Val Ile Asn Asp Tyr Phe
            515                 520                 525

Leu
```